(12) United States Patent
Culic et al.

(10) Patent No.: US 7,910,559 B2
(45) Date of Patent: Mar. 22, 2011

(54) DECLADINOSYL-MACROLIDES WITH ANTI-INFLAMMATORY ACTIVITY

(75) Inventors: Ognjen Culic, Zagreb (HR); Martina Bosnar, Zagreb (HR); Sulejman Alihodzic, Zagreb (HR); Gorjana Lazarevski, Zagreb (HR); Zorica Marusic Istuk, Zagreb (HR); Antun Hutinec, Zagreb (HR); Vanja Vela, Zagreb (HR); Goran Kragol, Zagreb (HR)

(73) Assignee: GlaxoSmithKline istrazivacki centar Zagreb d.o.o., Zagreb (HR)

( * ) Notice: Subject to any disclaimer, the term of this patent is extended or adjusted under 35 U.S.C. 154(b) by 684 days.

(21) Appl. No.: 11/813,876

(22) PCT Filed: Jan. 13, 2006

(86) PCT No.: PCT/IB2006/001097
§ 371 (c)(1),
(2), (4) Date: Oct. 8, 2007

(87) PCT Pub. No.: WO2006/077501
PCT Pub. Date: Jul. 27, 2006

(65) Prior Publication Data
US 2008/0234211 A1    Sep. 25, 2008

Related U.S. Application Data

(60) Provisional application No. 60/643,840, filed on Jan. 13, 2005.

(51) Int. Cl.
*A61K 31/70* (2006.01)
*C07H 17/08* (2006.01)

(52) U.S. Cl. .............................. 514/29; 536/7.2; 536/7.4

(58) Field of Classification Search ............ 536/7.2, 536/7.4
See application file for complete search history.

(56) References Cited

U.S. PATENT DOCUMENTS

| 5,631,354 A * | 5/1997 | Asaka et al. .......... 536/7.4 |
| 7,488,811 B2 * | 2/2009 | Napoletano et al. .......... 536/7.4 |

FOREIGN PATENT DOCUMENTS

| EP | 0 487 411 | 5/1992 |
| EP | 0 619 320 | 10/1994 |
| EP | 0 771 564 | 5/1997 |
| EP | 0 775 489 | 5/1997 |
| WO | 02/12260 | 2/2002 |
| WO | 2004/039821 | 5/2004 |

OTHER PUBLICATIONS

Tanikawa et al., "Synthesis and Antibacterial Activity of Acylides (3-0-Acyl-Erythromycin Derivatives): A Novel Class of Macrolide Antibiotics," Journal of Medicinal Chemistry, V44 N24, 2001, pp. 4027-4030.

* cited by examiner

*Primary Examiner* — Elli Peselev
(74) *Attorney, Agent, or Firm* — Karen L. Prus

(57) ABSTRACT

The present invention relates to novel semi-synthetic macrolides having anti-inflammatory activity. More particularly, the invention relates to 14- and 15-membered macrolides lacking cladinose sugar substituted at the C-3 position, to their pharmaceutically acceptable derivatives, to processes and intermediates for their preparation, to pharmaceutical compositions containing them and to their activity and use in the treatment of inflammatory diseases and conditions in humans and animals, especially those diseases associated with excessive secretion of TNF-$\alpha$, IL-1, IL-6, IL-8, IL-2 or IL-5; and/or inhibitor of excessive lymphocyte proliferation; and/or excessive granulocyte degranulation.

25 Claims, No Drawings

DECLADINOSYL-MACROLIDES WITH ANTI-INFLAMMATORY ACTIVITY

This application is filed pursuant to 35 U.S.C. §371 as a United States National Phase Application of International Application No. PCT/IB2006/001097 filed Jan. 13, 2006, which claims priority from U.S. 60/643,840 filed Jan. 13, 2005.

FIELD OF THE INVENTION

The present invention lies in the field of substituted macrolides having anti-inflammatory activity and methods of use thereof. More particularly, the invention relates to 14- and 15-membered macrolides lacking cladinose sugar substituted at the C-3 position, to their pharmaceutically acceptable derivatives, to processes and intermediates for their preparation, to pharmaceutical compositions containing them and to their activity and use in the treatment of inflammatory diseases and conditions in humans and animals, especially those diseases associated with excessive secretion of one or more of TNF-$\alpha$, IL-1, IL-6, IL-8, IL-2 or IL-5; and/or inhibitor of excessive lymphocyte proliferation; and/or excessive granulocyte degranulation.

BACKGROUND OF THE INVENTION

Inflammation is the final common pathway of various insults, such as infection, trauma, and allergies to the human body. It is characterized by activation of the immune system with recruitment of inflammatory cells, production of pro-inflammatory cells and production of pro-inflammatory cytokines.

Most inflammatory diseases are characterized by abnormal accumulation of inflammatory cells, including monocytes/macrophages, granulocytes, plasma cells, lymphocytes and platelets. Along with tissue endothelial cells and fibroblasts, these inflammatory cells release a complex array of lipids, growth factors, cytokines and destructive enzymes that cause local tissue damage.

One form of inflammatory response is neutrophilic inflammation which is characterized by infiltration of the inflamed tissue by neutrophil polymorphonuclear leucocytes (PMN), which are a major component of host defense. Tissue infection by extracellular bacteria represents the prototype of this inflammatory response. On the other hand, various non-infectious diseases are characterized by extravascular recruitment of neutrophils. This group of inflammatory diseases includes chronic obstructive pulmonary disease, adult respiratory distress syndrome, some types of immune-complex alveolitis, cystic fibrosis, bronchitis, bronchiectasis, emphysema, glomerulonephritis, rheumatoid arthritis, gouty arthritis, ulcerative colitis, certain dermatoses such as psoriasis and vasculitis. In these conditions neutrophils are thought to play a crucial role in the development of tissue injury which, when persistent, can lead to the irreversible destruction of the normal tissue architecture with consequent organ dysfunction. Tissue damage is primarily caused by the activation of neutrophils followed by their release of proteinases and increased production of oxygen species.

Chronic obstructive pulmonary disease (COPD) is described by the progressive development of airflow limitation that is not fully reversible (ATC, 1995). Most patients with COPD have three pathological conditions: bronchitis, emphysema and mucus plugging. This disease is characterized by a slowly progressive and irreversible decrease in forced expiratory volume in the first second of expiration (FEV$_1$), with relative preservation of forced vital capacity (FVC) (Barnes, *N. Engl. J. Med.* (2000), 343(4): 269-280). In both asthma and COPD there is significant, but distinct, remodeling of airways. Most of the airflow obstruction is due to two major components, alveolar destruction (emphysema) and small airways obstruction (chronic obstructive bronchitis). COPD is mainly characterized by profound mucus cell hyperplasia.

Cigarette smoking, air pollution and other environmental factors are major causes of the disease. The causal mechanism remains currently undefined but oxidant-antioxidant disturbances are strongly implicated in the development of the disease. COPD is a chronic inflammatory process that differs markedly from that seen in asthma, with different inflammatory cells, mediators, inflammatory effects and responses to treatment (Keatings et al., *Am. J. Respir. Crit. Care Med.* (1996), 153: 530-534). Neutrophil infiltration of the patient's lungs is a primary characteristic of COPD.

Elevated levels of proinflammatory cytokines like TNF-$\alpha$, and especially chemokines like IL-8 and GRO-$\alpha$ play a very important role in pathogenesis of this disease. Platelet thromboxane synthesis is also enhanced in patients with COPD (Keatings et al., *Am. J. Respir. Crit. Care Med.* (1996), 153: 530-534; Stockley and Hill, *Thorax* (2000), 55(7): 629-630). Most of the tissue damage is caused by activation of neutrophils followed by their release of (metallo)proteinases, and increased production of oxygen species (Repine et al., *Am. J. Respir. Crit. Care Med.* (1997), 156: 341-357; Barnes, *Chest* (2000), 117(2 Suppl): 10S-14S).

Most therapeutic endeavour is directed towards the control of symptoms (Barnes, *Trends Pharm. Sci.* (1998), 19(10): 415-423; Barnes, *Am. J. Respir. Crit. Care Med.* (1999) 160: S72-S79; Hansel et al., *Expert Opin. Investig. Drugs* (2000) 9(1): 3-23). Symptoms usually equate with airflow limitation and bronchodilators are the conventional therapy of choice. Prevention and treatment of complications, prevention of deterioration and improved quality and length of life are also primary goals stated in the three key international guidelines for the management of COPD (Culpitt and Rogers, *Exp. Opin. Pharmacother.* (2000) 1(5): 1007-1020; Hay, *Curr. Opin. Chem. Biol.* (2000), 4: 412-419). Basically, most of the current therapeutic research has been focused on mediators involved in the recruitment and activation of neutrophils, or attenuation of consequences of their undesirable activation (Stockley et al., *Chest* (2000), 117(2 Suppl.): 58S-62S).

In 1975, TNF-$\alpha$ was defined as an endotoxin-induced serum factor causing tumor necrosis in vitro and in vivo (Carswell E. A. et al. *Proc. Natl. Acad. Sci. U.S.A.* 1975, 72, 3666-3670). In addition to antitumor activity, TNF-$\alpha$ has several other biologic activities that are important in homeostasis as well as in pathophysiological conditions. The main sources of TNF-$\alpha$ are monocytes-macrophages, T-lymphocytes and mast cells.

The finding that anti-TNF-$\alpha$ antibodies (cA2) are effective in the treatment of patients suffering from rheumatoid arthritis (RA) (Elliot M. et al. *Lancet* 1994, 344, 1105-1110) intensified the interest to find new TNF-$\alpha$ inhibitors as possible potent medicaments for RA. Rheumatoid arthritis is an autoimmune chronic inflammatory disease characterized by irreversible pathological changes of the joints. In addition to RA, TNF-$\alpha$ antagonists are also applicable to several other pathological conditions and diseases such as spondylitis, osteoarthritis, gout and other arthritic conditions, sepsis, septic shock, toxic shock syndrome, atopic dermatitis, contact dermatitis, psoriasis, glomerulonephritis, lupus erythematosus, scleroderma, asthma, cachexia, chronic obstructive lung disease, congestive heart failure, insulin resistance, lung fibrosis, multiple sclerosis, Crohn's disease, ulcerative colitis, viral infections and AIDS.

The interest of the scientific community has recently turned towards the immunomodulating and anti-inflammatory activities of the macrolide antibiotics (*Journal of Antimicrobial Chemotherapy*, 1988, 41, Suppl. B, 37-46).

An ideal immunomodulating agent should be able to suppress the deleterious effects of the inflammatory response, while leaving the protective immune responses intact.

Macrolide antibiotics accumulate preferentially within different cells of subjects, especially within phagocyte cells such as mononuclear peripheral blood cells, and peritoneal and alveolar macrophages. (Gladue, R. P. et al, *Antimicrob. Agents Chemother.* 1989, 33, 277-282; Olsen, K. M. et al, *Antimicrob. Agents Chemother.* 1996, 40, 2582-2585). Anti-inflammatory effects of some macrolides have been described in the literature. For example, the anti-inflammatory effects of erythromycin derivatives have been described in *J. Antimicrob. Chemother.* 1998, 41, 37-46 and WO Patent Application No. 00/42055. Taisho claims further anti-inflammatory erythromycin derivatives modified in positions 3, 9, 11 and 12 (EP 0775489 and EP 0771564). In the patent application WO 02/087596, there is a good description of the anti-inflammatory activity of azithromycin, a known antibacterial agent. Azithromycin derivatives lacking the sugar moieties cladinose and desosamine and having anti-inflammatory activity have been described (Pliva, U.S. Pat. No. 4,886,792). International patent applications WO 04/039821 and WO 04/013153 (Zambon Group) disclose macrolide and azalide derivatives lacking cladinose sugar that exhibit anti-inflammatory but not antibacterial activity.

Anti-inflammatory effects of some macrolides are also known from in vitro and in vivo studies in experimental animal models such as in zymosan-induced peritonitis in mice (*J. Antimicrob. Chemother.* 1992, 30, 339-348) and endotoxin-induced neutrophil accumulation in rat trachea (*J. Immunol.* 1997, 159, 3395-4005). The modulating effect of macrolides upon cytokines such as interleukin 8 (IL-8) (*Am. J. Respir. Crit. Care. Med.* 1997, 156, 266-271) and interleukin 5 (IL-5) (EP Pat. No. 0775489 and EP Pat. No. 771564) is known as well.

Macrolides have proved to be useful in the treatment of inflammatory pathologies such as panbronchiolitis (Thorax, 1997, 52, 915-918), bronchial asthma (Chest, 1991, 99 670-673), and azithromycin in particular has proved effective in improving lung function in patients with cystic fibrosis (The Lancet, 1998, 351, 420).

The administration of macrolides to asthmatics is accompanied by a reduction in hypersecretion and in bronchial hypersensitivity resulting from the macrolides' anti-oxidative and anti-inflammatory interaction with phagocytes and in particular with neutrophils (Inflammation, Vol. 20, No. 6, 1996).

TECHNICAL PROBLEM

The invention is directed to solving the technical problem of providing novel targeted anti-inflammatory agents. More specifically, the invention provides anti-inflammatory agents wherein the active substance is neither a steroid nor an NSAID. The compounds of the invention are responsive to this problem by virtue of their anti-inflammatory activity and their ability to accumulate in various immune cells recruited to the locus of inflammation.

SUMMARY OF THE INVENTION

New 14- and 15-membered macrolide compounds lacking the cladinose sugar and substituted at the C-3 position, represented by the Formula (I), representing the subject of the present invention, their pharmaceutically acceptable derivatives and pharmaceutical compositions comprising them have hitherto not been described. Moreover, no compound representing the subject of the present invention has been described either as an anti-inflammatory substance or as an inhibitor of one or more of TNF-α, IL-1, IL-6, IL-8, IL-2 or IL-5; and/or inhibitor of excessive lymphocyte proliferation; and/or excessive granulocyte degranulation. Consequently, the use of such compounds to combat inflammatory states has not been described or suggested. Nor has there been a description or suggestion of pharmaceutical dosage forms containing effective amounts of a 14- or 15-membered macrolide compound lacking the cladinose sugar and substituted at the C-3 position for treating inflammatory states in a mammalian subject, including a human.

A characteristic of compounds represented by Formula (I) is selective accumulation in target organs and cells in the above mentioned inflammatory diseases and conditions. These pharmacokinetic properties enable the compounds represented by Formula (I) to act at the inflammation site in inflammation cells by inhibiting the production of inflammation mediators. In such a manner, the unfavourable systemic side-effects that are characteristic of corticosteroids or non-steroidal anti-inflammatory molecules are avoided and the therapeutic action of compounds represented by Formula (I) is targeted to the area where it is most needed. Following local or systemic application, molecules rapidly accumulate in inflammation cells wherein they act by inhibiting the production of cytokines and chemokines and/or other inflammatory mediators thus suppressing the inflammation.

Thus, the present invention is directed to:
(a) compounds represented by Formula (I)

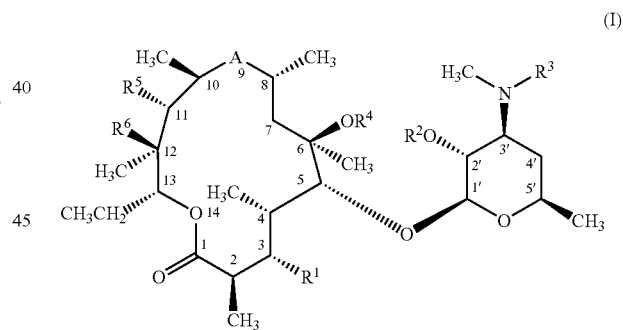

wherein
A is a bivalent radical selected from —C(O)—, —NHC(O)—, —C(O)NH—, —N($R^7$)$CH_2$—, —$CH_2$N($R^7$)—, —CH(OH)— and —C(=NO$R^7$)—;
$R^1$ is —OC(O)($CH_2$)$_n$N$R^8R^9$, —O—($CH_2$)$_n$N$R^8R^9$, or —OC(O)CH=$CH_2$;
$R^2$ is hydrogen or a hydroxyl protecting group;
$R^3$ is hydrogen, unsubstituted $C_{1-4}$ alkyl or $C_{1-4}$ alkyl substituted at terminal carbon atom with CN or $NH_2$ group, or $C_{1-5}$ alkanoyl;
$R^4$ is hydrogen, $C_{1-4}$ alkyl or $C_{2-6}$ alkenyl;
$R^5$ is hydroxy, methoxy, —OC(O)($CH_2$)$_n$N$R^8R^9$ or —O—($CH_2$)$_n$N$R^8R^9$;
$R^6$ is hydroxy; or
$R^5$ and $R^6$ taken together with the intervening atoms form a cyclic group having the following structure:

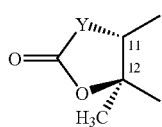

wherein Y is a bivalent radical selected from —CH$_2$—, —CH(CN)—, —O—, —N(R$^7$)— and —CH(SR$^7$)—;

R$^7$ is hydrogen or C$_{1-6}$ alkyl;

R$^8$ and R$^9$ are each independently hydrogen, C$_{3-7}$ cycloalkyl, C$_{1-18}$ alkyl, wherein C$_{1-18}$ alkyl is:
  i) uninterrupted or interrupted by from 1 to 3 bivalent radical groups selected from —O—, —S— and —N(R$^7$)—; and/or
  ii) unsubstituted or substituted by from 1 to 3 groups selected from halogen, OH, NH$_2$, N—(C$_1$-C$_6$)alkylamino, N,N-di(C$_1$-C$_6$-alkyl)amino, CN, NO$_2$, OCH$_3$, a C$_{3-8}$ membered non-aromatic ring which is saturated or unsaturated, a heterocyclic non-aromatic ring containing between 2 and 6 carbon atoms which is saturated or unsaturated and contains from 1 to 2 heteroatoms selected from oxygen, sulfur and nitrogen, alkylcarbonylalkoxy and alkoxycarbonylamino; or R$^8$ and R$^9$ taken together with the nitrogen to which they are attached form a non-aromatic heterocyclic ring containing between 2 and 6 carbon atoms which is:
  i) saturated or unsaturated and contains 0 or 1 additional heteroatoms selected from oxygen, sulfur and nitrogen; and/or
  ii) unsubstituted or substituted by from 1 to 2 groups selected from C$_{1-5}$ alkanoyl; C$_{1-6}$ alkyl, wherein C$_{1-6}$ alkyl is uninterrupted or is interrupted by 1-3 bivalent radical groups selected from —O—, —S— and —N(R$^7$)—, and/or wherein C$_{1-6}$ alkyl is unsubstituted or substituted by from 1 to 2 groups selected from OH, NH$_2$, a non-aromatic heterocyclic ring containing between 2 and 6 carbon atoms which is unsubstituted or is substituted by a group selected from C$_{1-4}$ alkyl, halogen, NH$_2$, OH, SH, C$_{1-6}$ alkoxy and C$_{1-4}$ hydroxyalkyl, and C$_{3-7}$ cycloalkyl which is unsubstituted or is substituted by a group selected from C$_{1-4}$ alkyl, halogen, NH$_2$, OH, SH, C$_{1-6}$ alkoxy, C$_{1-4}$ hydroxyalkyl; and C$_1$-C$_4$ dialkylamino;

n is an integer from 1 to 8 and pharmaceutically acceptable derivatives of the Formula (I) compounds;

(b) compositions containing one or more of the foregoing compounds in an amount effective to combat inflammation and thereby treat disorders and conditions involving inflammation in mammals, including humans; and (c) methods for using these compounds to treat such disorders and conditions.

DETAILED DESCRIPTION OF THE INVENTION

The phrase "pharmaceutically acceptable", as used in connection with compositions of the invention, refers to molecular entities and other ingredients of such compositions that are physiologically tolerable and do not typically produce untoward reactions when administered to a mammal (e.g., human). Preferably, as used herein, the term "pharmaceutically acceptable" means approved by a regulatory agency of the Federal or a state government or listed in the U.S. Pharmacopoeia or other generally recognized pharmacopoeia for use in mammals, and more particularly in humans.

The term "carrier" applied to pharmaceutical compositions of the invention refers to a diluents, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. However, since the macrolides are highly soluble, aqueous solutions are preferred. Suitable pharmaceutical carriers are described in "Remington's Pharmaceutical Sciences" by E. W. Martin, 18th Edition. Particularly preferred for the present invention are carriers suitable for immediate-release, i.e., release of most or all of the active ingredient over a short period of time, such as 60 minutes or less, and make rapid absorption of the drug possible.

The term "pharmaceutically acceptable derivative" as used herein means any pharmaceutically acceptable salt, solvate or prodrug, e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives. Preferred pharmaceutically acceptable derivatives are salts, solvates, esters, carbamates and phosphate esters. Particularly preferred pharmaceutically acceptable derivatives are salts, solvates and esters. Most preferred pharmaceutically acceptable derivatives are salts and esters.

The compounds of the present invention may be in the form of and/or may be administered as a pharmaceutically acceptable salt. For a review on suitable salts see Berge et al., J. Pharm. Sci., 1977, 66, 1-19.

Typically, a pharmaceutically acceptable salt may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of Formula (I) and the resulting mixture evaporated to dryness (lyophilized) to obtain the acid addition salt as a solid. Alternatively, a compound of Formula (I) may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

Suitable addition salts are formed from inorganic or organic acids which form non-toxic salts and examples are hydrochloride, hydrobromide, hydroiodide, sulfate, bisulphate, nitrate, phosphate, hydrogen phosphate, acetate, trifluoroacetate, maleate, malate, fumarate, lactate, tartrate, citrate, formate, gluconate, succinate, pyruvate, oxalate, oxaloacetate, trifluoroacetate, saccharate, benzoate, alkyl or aryl sulfonates (e.g. methanesulfonate, ethanesulfonate, benzenesulfonate or p-toluenesulfonate) and isethionate. Representative examples include trifluoroacetate and formate salts, for example the bis- or tris-trifluoroacetate salts and the mono or diformate salts, in particular the bis- or tris-trifluoroacetate salt and the monoformate salt.

Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Compounds of the invention may have both a basic and an acidic centre and may therefore be in the form of zwitterions.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The salts of a compound of Formula (I) may form solvates (e.g. hydrates) and the invention also includes all such solvates.

The term "prodrug" as used herein means a compound which is converted within the body, e.g. by hydrolysis in the blood, into its active form that has medicinal effects. Pharmaceutically acceptable prodrugs are described in T. Higuchi and V. Stella, "Prodrugs as Novel Delivery Systems", Vol. 14 of the A.C.S. Symposium Series, Edward B. Roche, ed., "Bioreversible Carriers in Drug Design", American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of Formula (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of one or more of alcohol, sulfhydryl and amine functional groups of the compounds of Formula (I). Further, in the case of a carboxylic acid (—COOH) group, esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

References hereinafter to a compound according to the invention include both compounds of Formula (I) and their pharmaceutically acceptable derivatives.

With regard to stereoisomers, the compounds of Formula (I) have more than one asymmetric carbon atom. In the general Formula (I) as drawn, solid wedge shaped bonds indicate that the bonds are above the plane of the paper. Broken bonds indicate that the bonds are below the plane of the paper.

It will be appreciated that the substituents on the macrolide may also have one or more asymmetric carbon atoms. Thus, the compounds of Formula (I) may occur as individual enantiomers or diastereomers. All such isomeric forms are included within the present invention, including mixtures thereof.

Where a compound of the invention contains an alkenyl group, cis (Z) and trans (E) isomerism may also occur. The present invention includes the individual stereoisomers of the compound of the invention and, where appropriate, the individual tautomeric forms thereof, together with mixtures thereof.

Separation of diastereoisomers or cis and trans isomers may be achieved by conventional techniques, e.g. by fractional crystallization, chromatography or H.P.L.C. An enantio- and diastereopure agent may also be prepared from a corresponding optically pure intermediate or by resolution, such as by H.P.L.C., of the corresponding racemate using a suitable chiral support or by fractional crystallisation of the diastereoisomeric salts formed by reaction of the corresponding racemate with a suitable optically active acid or base, as appropriate.

The compounds of Formula (I) may be in crystalline or amorphous form. Furthermore, some of the crystalline forms of the compounds of Formula (I) may exist as polymorphs, which are included in the present invention.

Compounds wherein $R^2$ represents a hydroxyl protecting group are in general intermediates for the preparation of other compounds of Formula (I).

When the group $OR^2$ is a protected hydroxyl group this is conveniently an ether or an acyloxy group. Examples of particularly suitable ether groups include those in which $R^2$ is a trialkylsilyl (i.e. trimethylsilyl). When the group $OR^2$ represents an acyloxy group, then examples of suitable groups $R^2$ include acetyl, benzoyl or benzyloxycarbonyl.

The term "alkyl" as used herein as a group or a part of a group refers to a straight or branched hydrocarbon chain containing the specified number of carbon atoms. For example, $C_{1-6}$ alkyl means a straight or branched alkyl chain containing from 1 to 6 carbon atoms; examples of such group include methyl, ethyl, propyl, isopropyl, n-butyl, isobutyl, tert-butyl, pentyl, 3-methyl-butyl, hexyl and 2,3-dimethylbutyl and the like.

When the alkyl chain is interrupted by from 1 to 3 of —O—, —S— or —N($R^7$)—, a methylene spacer can be present adjacent to an interrupting moiety. Thus, this would include, for example, —$CH_2$—O— and —O—$CH_2$—. When two or three of these interrupting moieties are present, they are separated by at least one methylene spacer.

The term "alkenyl" as used herein as a group or a part of a group refers to a straight or branched hydrocarbon chain containing the specified number of carbon atoms and containing at least one double bond. For example, the term "$C_{2-6}$ alkenyl" means a straight or branched alkenyl containing at least 2, and at most 6, carbon atoms and containing at least one double bond. Examples of "alkenyl" as used herein include, but are not limited to, ethenyl, 2-propenyl, 3-butenyl, 2-butenyl, 2-pentenyl, 3-pentenyl, 3-methyl-2-butenyl, 3-methylbut-2-enyl, 3-hexenyl and 1,1-dimethylbut-2-enyl. It will be appreciated that in groups of the form —O—$C_{2-6}$ alkenyl, the double bond is preferably not adjacent to the oxygen.

The term "$C_{1-5}$ alkanoyl" refers to acyl groups such as formyl, acetyl, propanoyl or butanoyl.

The term "halogen" refers to a fluorine, chlorine, bromine or iodine atom.

The term "$C_{3-7}$ cycloalkyl" group as used herein refers to a non-aromatic monocyclic hydrocarbon ring of 3 to 7 carbon atoms such as, for example, cyclopropyl, cyclobutyl, cyclopentyl, cyclohexyl or cycloheptyl.

The term "alkoxy" as used herein refers to a straight or branched chain alkoxy group containing the specified number of carbon atoms. For example, $C_{1-6}$ alkoxy means a straight or branched alkoxy containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy and hexyloxy.

The term "hydroxyalkyl" as used herein as a group refers to a straight or branched hydrocarbon chain containing the specified number of carbon atoms, which is substituted by 1-3 hydroxyl groups. For example, $C_{1-4}$ hydroxyalkyl means a straight or branched alkyl chain containing from 1 to 4 carbon atoms and at least one hydroxyl group; examples of such groups include, but are not limited to, hydroxymethyl, hydroxyethyl, hydroxypropyl, hydroxyisopropyl, hydroxybutyl and the like.

The term "heterocyclic" as used herein, unless otherwise defined, refers to a non-aromatic, saturated or unsaturated monocycle, containing two- to six carbon atoms and at least one heteroatom selected from oxygen, nitrogen and sulfur. Preferably, the heterocyclic ring has five to seven ring atoms. Examples of heterocyclic groups include, but are not limited to, pyrrolidinyl, tetrahydrofuranyl, tetrahydrothiophenyl, imidazolidinyl, pyrazolidinyl, piperidinyl, piperazinyl, homopiperazinyl, morpholinyl, tetrahydropyranyl and thiomorpholinyl.

The term "leaving group" refers to a chemical group which is capable of being displaced by a nucleophile. Examples of such groups include but are not limited to halogen, mesylate, tosylate and ester groups.

In some preferred embodiments, this invention relates to the compounds of Formula (I) and to pharmaceutically acceptable derivatives thereof wherein A represents —NHC(O)— or —C(O)NH—. Within this subset, all other variables are as originally defined.

Another preferred aspect of the invention relates to the compounds of Formula (I) and to pharmaceutically acceptable derivatives thereof wherein A represents —N($R^7$)$CH_2$— or —$CH_2$N($R^7$)—. Within this subset, all other variables are as originally defined.

Yet another preferred aspect of the invention relates to the compounds of Formula (I) and to pharmaceutically acceptable derivatives thereof wherein A represents —C(O)—, —CH(OH)—, or —C(—$NOR^7$)—. Within this subset, all other variables are as originally defined.

Representative examples of $R^3$ include hydrogen, unsubstituted $C_{1-4}$ alkyl, for example methyl and $C_{1-5}$ alkanoyl, for example acetyl.

A preferred aspect of the invention relates to the compounds of Formula (I) and to pharmaceutically acceptable derivatives thereof wherein $R^4$ is hydrogen or methyl.

In one embodiment, $R^5$ and $R^6$ are hydroxy. Alternatively, $R^5$ and $R^6$ taken together with the intervening atoms form a cyclic group having the following structure:

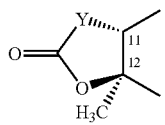

wherein Y is a bivalent radical selected from —O— and —N($R^7$)—.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used herein includes both one and more than one such excipient.

"Treating" or "treatment" of a state, disorder or condition includes:

(1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms.

The benefit to a subject to be treated is either statistically significant or at least perceptible to the patient or to the physician.

A "therapeutically effective amount" means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The four classic symptoms of acute inflammation are redness, elevated temperature, swelling and pain in the affected area, and loss of function of the affected organ.

Symptoms and signs of inflammation associated with specific conditions include:

rheumatoid arthritis—pain, swelling, warmth and tenderness of the involved joints; generalized and morning stiffness;

insulin-dependent diabetes mellitus—insulitis; this condition can lead to a variety of complications with an inflammatory component, including: retinopathy, neuropathy, nephropathy; coronary artery disease, peripheral vascular disease, and cerebrovascular disease;

autoimmune thyroiditis—weakness, constipation, shortness of breath, puffiness of the face, hands and feet, peripheral edema, bradycardia;

multiple sclerosis—spasticity, blurry vision, vertigo, limb weakness, paresthesias;

uveoretinitis—decreased night vision, loss of peripheral vision;

lupus erythematosus—joint pain, rash, photosensitivity, fever, muscle pain, puffiness of the hands and feet, abnormal urinalysis (hematuria, cylinduria, proteinuria), glomerulonephritis, cognitive dysfunction, vessel thrombosis, pericarditis;

scleroderma—Raynaud's disease; swelling of the hands, arms, legs and face; skin thickening; pain, swelling and stiffness of the fingers and knees, gastrointestinal dysfunction, restrictive lung disease; pericarditis; renal failure;

other arthritic conditions having an inflammatory component such as rheumatoid spondylitis, osteoarthritis, septic arthritis and polyarthritis—fever, pain, swelling, tenderness;

other inflammatory brain disorders, such as meningitis, Alzheimer's disease, AIDS dementia encephalitis—photophobia, cognitive dysfunction, memory loss;

other inflammatory eye inflammations, such as retinitis—decreased visual acuity;

inflammatory skin disorders, such as, eczema, other dermatites (e.g., atopic, contact), psoriasis, burns induced by UV radiation (sun rays and similar UV sources)—erythema, pain, scaling, swelling, tenderness;

inflammatory bowel disease, such as Crohn's disease, ulcerative colitis—pain, diarrhea, constipation, rectal bleeding, fever, arthritis;

asthma—shortness of breath, wheezing;

other allergy disorders, such as allergic rhinitis—sneezing, itching, runny nose conditions associated with acute trauma such as cerebral injury following stroke—sensory loss, motor loss, cognitive loss;

heart tissue injury due to myocardial ischemia—pain, shortness of breath;

lung injury such as that which occurs in adult respiratory distress syndrome—shortness of breath, hyperventilation, decreased oxygenation, pulmonary infiltrates;

inflammation accompanying infection, such as sepsis, septic shock, toxic shock syndrome—fever, respiratory failure, tachycardia, hypotension, leukocytosis, osteomyelitis;

other inflammatory conditions associated with particular organs or tissues, such as nephritis (e.g., glomerulonephritis)—liguria, abnormal urinalysis;

inflamed appendix—fever, pain, tenderness, leukocytosis;

gout—pain, tenderness, swelling and erythema of the involved joint, elevated serum and/or urinary uric acid;

inflamed gall bladder—abdominal pain and tenderness, fever, nausea, leukocytosis;

chronic obstructive pulmonary disorder (COPD)—shortness of breath, wheezing;

congestive heart failure—shortness of breath, rates, peripheral edema chronic sinusitis, nasal polyps; cystic fibrosis; diffuse panbronchiolitis; bronchiectasis; bronchiolitis obliterans;

Type II diabetes—end organ complications including cardiovascular, ocular, renal, and peripheral vascular disease lung fibrosis—hyperventilation, shortness of breath, decreased oxygenation;

vascular disease, such as coronary artery disease, atherosclerosis and restenosis—pain, loss of sensation, diminished pulses, loss of function; and alloimmunity leading to transplant rejection—pain, tenderness, fever.

Symptoms associated with COPD have been outlined supra.

Subclinical symptoms include without limitation diagnostic markers for inflammation, the appearance of which may precede the manifestation of clinical symptoms. One class of subclinical symptoms is immunological symptoms, such as the invasion or accumulation in an organ or tissue of pro-inflammatory lymphoid cells or the presence locally or peripherally of activated pro-inflammatory lymphoid cells recognizing a pathogen or an antigen specific to the organ or tissue and secreting or inducing pro-inflammatory cytokines. Activation of lymphoid cells can be measured by techniques known in the art.

"Delivering" a therapeutically effective amount of an active ingredient to a particular location within a host means causing a therapeutically effective blood concentration of the active ingredient at the particular location. This can be accomplished, e.g., by local or by systemic administration of the active ingredient to the host.

The term "host" or "subject" as used herein refers to a mammal preferably a human.

Preferred compounds of the invention are the compounds of examples 1-27 and pharmaceutically acceptable derivatives thereof.

Methods of Preparation:

Compounds of Formula (I) and pharmaceutically acceptable derivatives thereof may be prepared by the general methods outlined hereinafter, said methods constituting a further aspect of the invention. In the following description, the groups $R^1$ to $R^9$, A and n, have the meaning defined for the compounds of Formula (I) unless otherwise stated.

It will be obvious to a person skilled in the art that, in order to avoid interference with any functional groups other than those where structural modifications are to be made, appropriate protection and priority in the synthetic route should be chosen. A comprehensive discussion of the ways in which functional groups may be protected and methods for cleaving the resulting protected derivatives is given by, for example, T. W. Greene and P. G. M Wuts in Protective Groups in Organic Synthesis $2^{nd}$ ed., John Wiley & Son, Inc 1991 and by P. J. Kocienski in Protecting Groups, Georg Thieme Verlag 1994 which are incorporated herein by reference.

The synthesis of the target compound is completed by removing any protecting groups present in the penultimate intermediate using standard techniques, which are well known to those skilled in the art. The deprotected final product is then purified, as necessary, using standard techniques such as silica gel chromatography, HPLC on silica gel, and the like or by recrystallization.

The group $-NR^{8a}R^{9a}$ in the following synthetic paths is $-NR^8R^9$ as defined for Formula (I) or a group convertible to $-NR^8R^9$ (e.g., a protected amine functionality). Conversion of a group $-NR^{8a}R^{9a}$ to a $-NR^8R^9$ group typically arises if a protecting group is needed during the reactions described below. Examples of suitable amino protecting groups include acyl type protecting groups (e.g. formyl, trifluoroacetyl and acetyl), aromatic urethane type protecting groups (e.g. benzyloxycarbonyl (Cbz) and substituted Cbz, and 9-fluorenylmethoxycarbonyl (Fmoc)), aliphatic urethane protecting groups (e.g. t-butyloxycarbonyl (Boc), isopropyloxycarbonyl and cyclohexyloxycarbonyl) and alkyl type protecting groups (e.g. benzyl, trityl and chlorotrityl). Examples of suitable oxygen protecting groups may include for example alkyl silyl groups, such as trimethylsilyl or tert-butyldimethylsilyl; alkyl ethers such as tetrahydropyranyl or tert-butyl; or esters such as acetate. Hydroxy groups may be protected by reaction of for example acetic anhydride, benzoic anhydride or a trialkylsilyl chloride in an aprotic solvent. Examples of aprotic solvents are dichloromethane, N,N-dimethylformamide, dimethylsulfoxide, tetrahydrofuran and the like.

The compounds of Formula (I) wherein $R^1$ is $OC(O)(CH_2)_n NR^8R^9$ and n is an integer from 1 to 8 may be prepared by reaction of the compounds of Formula (II) wherein $R^2$ is a hydroxy protecting group, with carboxylic acid (III) or a suitable activated derivative of the carboxylic acid (III), followed where necessary by subsequent removal of the hydroxyl protecting group $R^1$ and conversion of the $-NR^{8a}R^{9a}$ group to $-NR^8R^9$. Similarly, intermediate compounds related to the compounds of Formula (I) wherein $R^1$ is $-OC(O)(CH_2)_n NR^8R^9$ and $R^3$ is $CH_3$ may be prepared by the same method.

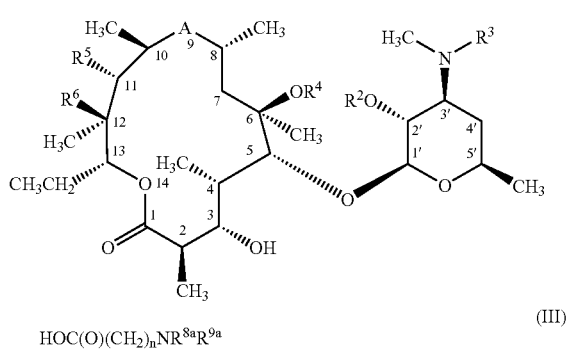

(II)

(III)

$HOC(O)(CH_2)_nNR^{8a}R^{9a}$

Suitable activated derivatives of the carboxylic acid include the corresponding acyl halide, mixed anhydride or activated ester such as a thiol ester.

The reaction is preferably carried out in a suitable aprotic solvent such as a halohydrocarbon (e.g. dichloromethane) or N,N-dimethylformamide optionally in the presence of a tertiary base such as dimethylaminopyridine or triethylamine or in the presence of inorganic base (e.g. sodium hydroxide) and at a temperature within the range of 0° to 120° C. The compounds of Formula (II) and (III) may also be reacted in the presence of a carbodiimide such as dicyclohexylcarbodiimide (DCC).

Compounds of Formula (II) are prepared according to a well-known process described, for example, in J. Chem. Soc. Perkin Trans. 1 (1986) 1881-1890 and WO 9951616, by acid-catalyzed cleavage of the cladinose sugar.

In a further embodiment of the invention, compounds of Formula (I) wherein $R^1$ is $OC(O)(CH_2)_nNR^8R^9$ and n is an integer from 1 to 8 may be prepared by reaction of the compounds of Formula (IV), wherein n is an integer from 1 to 8 and L is a suitable leaving group, with $HNR^{8a}R^{9a}$ (V).

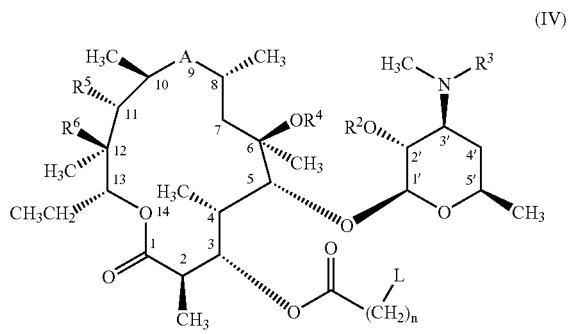

(IV)

The reaction is preferably carried out in a solvent such as a halohydrocarbon (e.g. dichloromethane), an ether (e.g. tetrahydrofuran or dimethoxyethane), acetonitrile or ethyl acetate and the like, dimethylsulfoxide, N,N-dimethylformamide or 1-methyl-pyrrolidone and in the presence of a base, followed, if desired, by removal of the hydroxyl protecting group $R^2$ and conversion of the $-NR^{8a}R^{9a}$ group to $-NR^8R^9$. Examples of the bases which may be used include organic bases such as diisopropylethylamine, triethylamine and 1,8-diazabicyclo[5.4.0]undec-7-ene, and inorganic bases such as potassium hydroxide, cesium hydroxide, tetraalkylammonium hydroxide, sodium hydride, potassium hydride and the like. Suitable leaving groups for this reaction include halide (e.g. chloride, bromide or iodide) or a sulfonate group (e.g. tosylate, methanesulfonate, or triflate).

Compounds of Formula (IV) may be prepared by reaction of a compound of Formula (II), wherein $R^2$ is a hydroxyl protecting group, with carboxylic acid $HOC(O)(CH_2)_nL$ (VI) or a suitable activated derivative of the carboxylic acid, wherein L is a suitable leaving group as defined in the previous paragraph. Suitable activated derivatives of the carboxyl group are those defined above for carboxylic acid (III). The reaction is carried out using the conditions described above for the reaction of a compound of Formula (II) with carboxylic acid (III).

In a preferred embodiment of the invention, compounds of Formula (I) wherein $R^1$ is $OC(O)(CH_2)_nNR^8R^9$ and n is 2 may be prepared by Michael reaction of the compounds of Formula (VII) wherein $R^2$ is a hydroxy protecting group with a compound of Formula $HNR^{8a}R^{9a}$ (V).

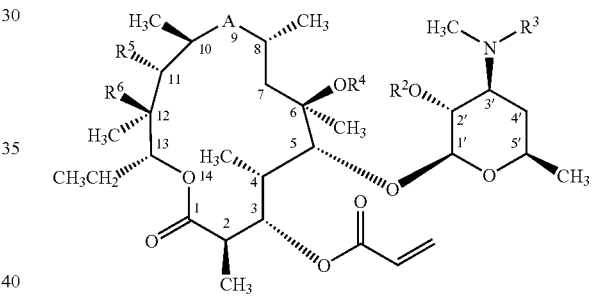

(VII)

The reaction is suitably carried out in a solvent such as dimethylsulfoxide, N,N-dimethylformamide, 1-methyl-pyrrolidone, a halohydrocarbon (e.g. dichloromethane), an ether (e.g. tetrahydrofuran or dimethoxyethane), acetonitrile or alcohol (e.g. methanol or isopropanol) and the like, and in the presence of a base, followed, if desired, by removal of hydroxyl protecting group $R^2$ and conversion of the $-NR^{8a}R^{9a}$ group to $-NR^8R^9$.

Compounds of Formula (VII) can be prepared according to the procedure described in international patent application WO 03/042228 incorporated by reference herein in its entirety, especially pages 16-18. Thus, reaction of the compounds of Formula (II) wherein $R^1$ is a hydroxy protecting group with 3-chloropropionyl chloride in the presence of a base such as triethylamine gives compounds of Formula (VII).

Compounds of Formula (I) wherein $R^1$ is $-O-(CH_2)_n NR^8R^9$ may be prepared by reaction of a 3-O-aldehyde compound of Formula (VIII), wherein n is an integer from 1 to 8, with a compound of Formula $HNR^{8a}R^{9a}$ (V), followed where necessary by subsequent removal of the protecting groups and conversion of the $NR^{8a}R^{9a}$ to $NR^8R^9$.

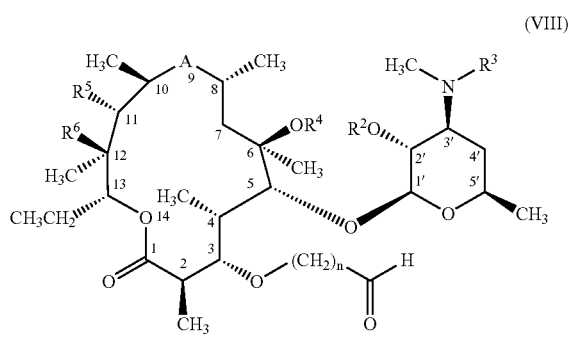
(VIII)

The reductive amination reaction is preferably carried out in a solvent such as methanol and DMF. A suitable reducing agent is, for example, sodium cyanoborohydride.

Compounds of Formula (VIII) where n is 1 or 2 may be prepared from suitably protected compounds of Formula (IX) by hydroboration with 9-BBN, or other suitable boranes, followed by treatment with peroxide and then oxidation (n=2), or by osmium tetroxide/periodate cleavage (n=1).

Compounds of Formula (IX) can be formed by palladium-catalyzed allylation (Recl. Trav. Chim. Pays-Bas 102, 501-505, 1983) of the C-3-hydroxy compounds of Formula (II) that are suitably protected, for example, by cyclic protection between the 9 and 11 positions when A is —C(OH)— (J. Antibiot., 42, 293, 1989.).

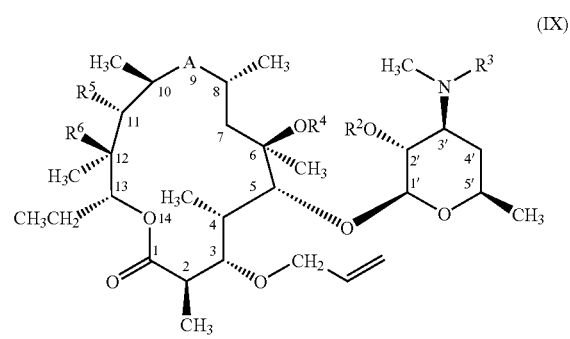
(IX)

In a further embodiment of the invention, compounds of Formula (I) wherein $R^1$ is —O—$(CH_2)_n NR^8R^9$ may be prepared by reaction of compounds of Formula (X) with a

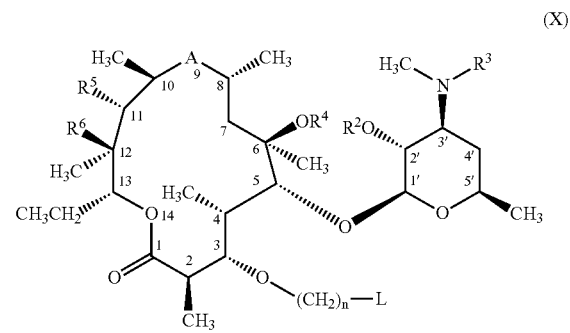
(X)

compound of Formula $HNR^{8a}R^{9a}$ (V), wherein n is an integer from 2 to 8 and L is a suitable leaving group as described for the compounds of Formula (IV). The reaction is preferably carried out in a solvent such as a halohydrocarbon (e.g. dichloromethane), an ether (e.g. tetrahydrofuran or dimethoxyethane), acetonitrile or ethyl acetate and the like, dimethylsulfoxide, N,N-dimethylformamide or 1-methylpyrrolidone and in the presence of a base, followed, if desired, by removal of protecting group $R^2$ and conversion of the $NR^{8a}R^{9a}$ group to $NR^8R^9$. Examples of the bases which may be used include organic bases such as diisopropylethylamine, triethylamine and 1,8-diazabicyclo[5.4.0]undec-7-ene (DBU), and inorganic bases such as potassium hydroxide, cesium hydroxide, tetraalkylammonium hydroxide, sodium hydride, potassium hydride and the like. Suitable leaving groups for this reaction are halide (e.g. chloride, bromide or iodide).

In a further embodiment of the invention, compounds of Formula (I) wherein $R^1$ is —O—$(CH_2)_n NR^8R^9$, n is 3, and $R^8$ and $R^9$ are the same and have the meaning as defined above, may be prepared by reductive amination of C-3-amine of Formula (XI) wherein Z is $CH_2NH_2$ with a compound of Formula $HC(O)R^8$ (XII).

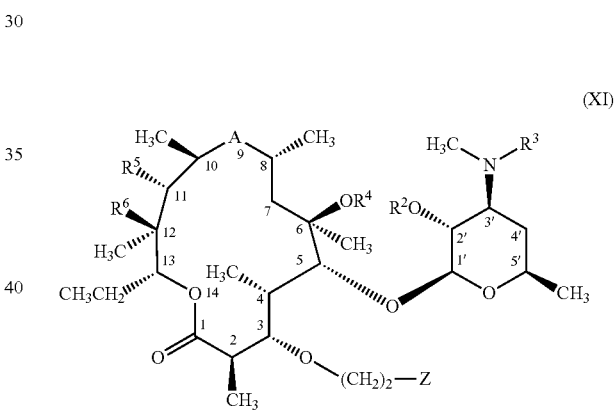
(XI)

Compounds of Formula (XI) wherein Z is $CH_2NH_2$ may be prepared by reaction of a suitable protected compound of Formula (II) with acrylonitrile in solvent such as DMSO, THF, t-BuOH in the presence of a base such as NaH giving compound of Formula (XI) wherein Z is a cyano group, followed by catalytic reduction of the cyano group to an amino group.

Compounds of Formula (II) wherein A is —C(=$NOR^7$) and $R^7$ is hydrogen are known compounds or they can be prepared starting from compounds of Formula (IIa) wherein A is —C(=$NOR^7$) and $R^7$ is hydrogen (U.S. Pat. No. 3,478,014 or *Journal of Antibiotics*, 44, 313, 1991), according to well known processes described, for example, in J. Chem. Soc. Perkin Trans. 1 (1986) 1881-1890 and WO 9951616, by acid-catalyzed cleavage of the cladinose sugar. Compounds wherein $R^7$ is other than a hydrogen atom can be prepared by alkylation of the oxime, for example, according to EP 1167375.

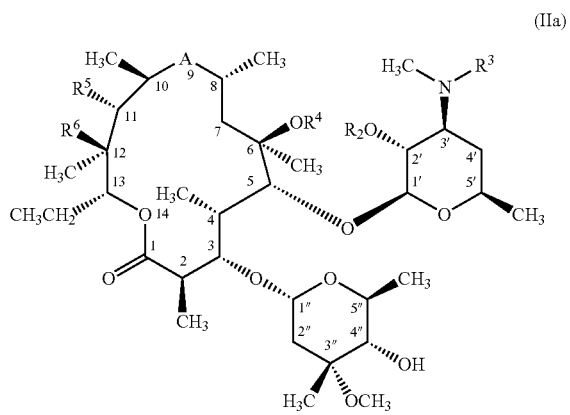

(IIa)

Compounds of Formula (II) wherein A is —CH(OH)— can be prepared starting from compounds of Formula (IIa) wherein A is —CH(OH)— (JACS 79, 6062, 1957, *Journal of Antibiotics* 43. 1334, 1990) by acid catalyzed cleavage of the cladinose sugar.

Compounds of Formula (II) wherein A is —NHC(O)— or —C(O)NH— and $R^4$ is $C_{1-4}$ alkyl or $C_{2-6}$ alkenyl are known compounds or they may be prepared from corresponding 6-O-alkyl or alkenylerythromycin A oxime by Beckman rearrangement according to the procedure described in WO 99/51616 followed by acid catalyzed cleavage of cladinose sugar.

Compounds of Formula (II) wherein A is —$NR^7CH_2$— or —$CH_2N(R^7)$— are known compounds or they may be prepared starting from compounds of Formula (IIa) wherein A is —$NR^7CH_2$— or —$CH_2N(R^7)$— (U.S. Pat. No. 4,328,334, BE 892357, U.S. Pat. No. 4,464,527, *Bioorg. Med. Chem. Lett.*, 3, 1287, 1993) by analogous methods described in the previous paragraph.

Compounds of Formula (II) wherein $R^3$ is hydrogen, $C_{2-4}$ alkyl or $C_{1-5}$ alkanoyl are prepared starting from compounds of Formula (IIa) wherein $R^3$ is methyl, by mono-demethylation of the 3'-$NMe_2$ group with benzylchloroformate, followed by elimination of benzyloxycarbonyl groups at positions 2' and 3' as described in U.S. Pat. No. 5,250,518. An alternative method for demethylation of the 3'-$NMe_2$ group is treatment with sodium acetate and iodine in the presence of an organic solvent, as described in U.S. Pat. No. 3,725,385 and WO 2004/013153. The subsequent alkylation or acylation of the secondary amine thus obtained is carried out in accordance with conventional synthetic techniques and by subsequent acid catalyzed cleavage of the cladinose sugar according to the procedure described in WO 99/51616.

Compounds of Formula (II) wherein $R^5$ and $R^6$ taken together with the intervening atoms form a cyclic group having the following structure:

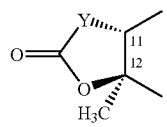

wherein Y is a bivalent radical selected from —$CH_2$—, —CH(CN)—, —O—, —$N(R^7)$— and —$CH(SR^7)$—; may be prepared starting from compounds of Formula (IIa) wherein $R^5$ and $R^6$ taken together with the intervening atoms form a cyclic group having the following structure:

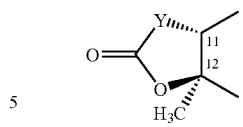

wherein Y is a bivalent radical selected from —$CH_2$—, —CH(CN)—, —O—, —$N(R^7)$— and —$CH(SR^7)$— by analogous methods known to those skilled in the art, for example according to the procedure described in WO 2004/039822, followed by acid catalyzed cleavage of the cladinose sugar according to the procedure described in WO 99/51616.

A further aspect of the present invention relates to the methods for using the compounds of Formula (I) as anti-inflammatory, anti-anaphylactic and immunomodulating agents which can be administered in different ways, depending on the inflammation site, e.g. percutaneously, orally, buccally, rectally, parenterally or by inhalation when application within the respiratory tract is intended.

The corresponding preparations of the compounds of the present invention can be used in the prophylaxis as well as in the therapeutic treatment (prevention, delay, inhibition or relief) of several disorders (diseases and other pathological inflammatory conditions) caused by or associated with an abnormal or undesirable (excessive, nonregulated, or dysregulated) inflammatory immune response involving the production of inflammatory cytokines or other inflammation mediators, including without limitation TNF-α, IL-1, IL-6, IL-8, IL-2 or IL-5, and/or the inhibition of excessive lymphocyte proliferation, and/or excessive granulocyte degranulation. These disorders include autoimmune diseases such as rheumatoid arthritis, insulin-dependent diabetes mellitus, autoimmune thyroiditis, multiple sclerosis, uveoretinitis, lupus erythematosus, scleroderma; psoriasis, acne; other arthritic conditions having an inflammatory component such as rheumatoid spondylitis, osteoarthritis, osteomyelitis; septic arthritis and polyarthritis; other inflammatory brain disorders, such as meningitis, Alzheimer's disease, AIDS dementia encephalitis, other inflammatory eye inflammations, such as retinitis; inflammatory skin disorders, such as eczema, other dermatites (e.g., atopic, contact), psoriasis, burns induced by UV radiation (sun rays and similar UV sources); inflammatory bowel disease, such as Crohn's disease, ulcerative colitis; COPD; cystic fibrosis; bronchiectasis; asthma; other allergy disorders, such as allergic rhinitis; chronic sinusitis; conditions associated with acute trauma such as cerebral injury following stroke, heart tissue injury due to myocardial ischemia, lung injury such as that which occurs in adult respiratory distress syndrome; inflammation accompanying infection, such as sepsis, septic shock, toxic shock syndrome, other inflammatory conditions associated with particular organs or tissues, such as nephritis (e.g., glomerulonephritis), inflamed appendix, gout, inflamed gall bladder, congestive heart failure, Type II diabetes, lung fibrosis, bronchiolitis obliterans; diffuse panbronchiolitis; vascular disease, such as coronary artery disease, atherosclerosis and restenosis; and alloimmunity leading to transplant rejection. The compounds can also be administered by inhalation when application within the respiratory tract is intended. A further object of the present invention relates to the preparation of various pharmaceutical forms of the compounds to achieve the optimal bioavailability of the active compounds of Formula (I).

Pharmaceutical Compositions

Further, the present invention relates to pharmaceutical compositions containing an effective dose of compounds of the present invention as well as pharmaceutically acceptable excipients, such as carriers or diluents.

While it is possible that, for use in the methods of the invention, the compounds of Formula I may be administered as the bulk substance, it is preferable to present the active ingredient in a pharmaceutical formulation, e.g., wherein the agent is in admixture with a pharmaceutically acceptable carrier selected with regard to the intended route of administration and standard pharmaceutical practice.

The corresponding preparations of the compounds of the present invention can be used in the prophylaxis (including without limitation the prevention, delay or inhibition of recurrence of one or more of the clinical or subclinical symptoms discussed and defined in connection with the definitions of "treatment" above, as well as in the therapeutic treatment of several diseases and pathological inflammatory conditions including: chronic obstructive pulmonary disorder (COPD), asthma, inflammatory nasal diseases such as allergic rhinitis, nasal polyps, intestinal diseases such as Crohn's disease, colitis, intestinal inflammation, ulcerative colitis, dermatological inflammations such as eczema, psoriasis, allergic dermatitis, neurodermatitis, pruritis, conjunctivitis and rheumatoid arthritis.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

It will be appreciated that pharmaceutical compositions for use in accordance with the present invention may be in the form of oral, parenteral, transdermal, inhalation, sublingual, topical, implant, nasal, or enterally administered (or other mucosally administered) suspensions, capsules or tablets, which may be formulated in conventional manner using one or more pharmaceutically acceptable carriers or excipients.

There may be different composition/formulation requirements depending on the different delivery systems. It is to be understood that not all of the compounds need to be administered by the same route. Likewise, if the composition comprises more than one active component, then those components may be administered by the same or different routes. By way of example, the pharmaceutical composition of the present invention may be formulated to be delivered using a mini-pump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by multiple routes.

The present invention further relates to pharmaceutical formulations containing a therapeutically effective quantity of a compound of Formula I or one of its salts mixed with a pharmaceutically acceptable vehicle. The pharmaceutical formulations of the present invention can be liquids that are suitable for oral, mucosal and/or parenteral administration, for example, drops, syrups, solutions, injectable solutions that are ready for use or are prepared by the dilution of a freeze-dried product but are preferably solid or semisolid as tablets, capsules, granules, powders, pellets, pessaries, suppositories, creams, salves, gels, ointments; or solutions, suspensions, emulsions, or other forms suitable for administration by the transdermal route or by inhalation.

The compounds of the invention can be administered for immediate-, delayed-, modified-, sustained-, pulsed- or controlled-release applications.

The compound can also be incorporated into a formulation for treating inflammation localized in an organ or tissue, e.g., Crohn's disease, where it can be administered orally or rectally. Formulations for oral administration can incorporate excipients enabling bioavailability of the compound at the site of inflammation. This can be achieved by different combinations of enteric and delayed release formulations. A compound of Formula I can also be used in the treatment of Crohn's disease and intestinal inflammation disease if the compound is applied in the form of a clyster, for which a suitable formulation can be used, as is well known in the field.

In some embodiments, the oral compositions are slow, delayed or positioned release (e.g., enteric especially colonic release) tablets or capsules. This release profile can be achieved without limitation by use of a coating resistant to conditions within the stomach but releasing the contents in the colon or other portion of the GI tract wherein a lesion or inflammation site has been identified. Or a delayed release can be achieved by a coating that is simply slow to disintegrate. Or the two (delayed and positioned release) profiles can be combined in a single formulation by choice of one or more appropriate coatings and other excipients. Such formulations constitute a further feature of the present invention.

Formulations for oral administration can be so designed to enable bioavailability of the compound at the site of inflammation in the intestines. This can be achieved by different combinations of delayed release formulations. A compound of Formula I can also be used in the treatment of Crohn's disease and intestinal inflammation disease if the compound is applied in the form of an enema, for which a suitable formulation can be used.

Suitable compositions for delayed or positioned release and/or enteric coated oral formulations include tablet formulations film coated with materials that are water resistant, pH sensitive, digested or emulsified by intestinal juices or sloughed off at a slow but regular rate when moistened. Suitable coating materials include, but are not limited to, hydroxypropyl methylcellulose, ethyl cellulose, cellulose acetate phthalate, polyvinyl acetate phthalate, hydroxypropyl methylcellulose phthalate, polymers of methacrylic acid and its esters, and combinations thereof. Plasticizers such as, but not limited to polyethylene glycol, dibutylphthalate, triacetin and castor oil may be used. A pigment may also be used to color the film. Suppositories are be prepared by using carriers like cocoa butter, suppository bases such as Suppocire C, and Suppocire NA50 (supplied by Gattefossé Deutschland GmbH, D-Weil am Rhein, Germany) and other Suppocire type excipients obtained by interesterification of hydrogenated palm oil and palm kernel oil (C8-C18 triglycerides), esterification of glycerol and specific fatty acids, or polyglycosylated glycerides, and whitepsol (hydrogenated plant oils derivatives with additives). Enemas are formulated by using the appropriate active compound according to the present invention and solvents or excipients for suspensions. Suspensions are produced by using micronized compounds, and appropriate vehicle containing suspension stabilizing agents, thickeners and emulsifiers like carboxymethylcellulose and salts thereof, polyacrylic acid and salts thereof, carboxyvinyl polymers and salts thereof, alginic acid and salts thereof, propylene glycol alginate, chitosan, hydroxypropylcellulose, hydroxypropylmethylcellulose, hydroxyethylcellulose, ethylcellulose, methylcellulose, polyvinyl alcohol, polyvinyl pyrrolidone, N-vinylacetamide polymer, polyvinyl methacrylate, polyethylene glycol, pluronic, gelatin, methyl vinyl ether-maleic anhydride copolymer, soluble starch, pullulan and a copolymer of methyl acrylate and 2-ethylhexyl acrylate lecithin, lecithin derivatives, propylene glycol fatty acid esters, glycerin fatty acid esters, sorbitan fatty acid esters, polyoxyethylene sorbitan fatty acid esters, polyethylene glycol fatty acid esters, polyoxyethylene hydrated caster oil, polyoxyethylene alkyl ethers, and pluronic and appropriate buffer system in pH range of 6.5 to 8. The use of preservatives, masking agents is suitable. The average diameter of micronized particles can be between 1 and 20 micrometers, or can be less than 1 micrometer. Compounds can also be incorporated in the formulation by using their water-soluble salt forms.

Alternatively, materials may be incorporated into the matrix of the tablet e.g. hydroxypropyl methylcellulose, ethyl cellulose or polymers of acrylic and methacrylic acid esters. These latter materials may also be applied to tablets by compression coating.

Pharmaceutical compositions can be prepared by mixing a therapeutically effective amount of the active substance with a pharmaceutically acceptable carrier that can have different forms, depending on the way of administration. Pharmaceutical compositions can be prepared by using conventional pharmaceutical excipients and methods of preparation. The forms for oral administration can be capsules, powders or tablets where usual solid vehicles including lactose, starch, glucose, methylcellulose, magnesium stearate, di-calcium phosphate, mannitol may be added, as well as usual liquid oral excipients including, but not limited to, ethanol, glycerol, and water. All excipients may be mixed with disintegrating agents, solvents, granulating agents, moisturizers and binders. When a solid carrier is used for preparation of oral compositions (e.g., starch, sugar, kaolin, binders disintegrating agents) preparation can be in the form of powder, capsules containing granules or coated particles, tablets, hard gelatin capsules, or granules without limitation, and the amount of the solid carrier can vary (between 1 mg to 1 g). Tablets and capsules are the preferred oral composition forms.

Pharmaceutical compositions containing compounds of the present invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

Examples of pharmaceutically acceptable disintegrants for oral compositions useful in the present invention include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and crosslinked polyvinylpyrrolidone.

Examples of pharmaceutically acceptable binders for oral compositions useful herein include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral compositions include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulfate.

Examples of pharmaceutically acceptable lubricants useful in the compositions of the invention include, but are not limited to, magnesium stearate, talc, polyethylene glycol, polymers of ethylene oxide, sodium lauryl sulfate, magnesium lauryl sulfate, sodium oleate, sodium stearyl fumarate, and colloidal silicon dioxide.

Examples of suitable pharmaceutically acceptable odorants for the oral compositions include, but are not limited to, synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral compositions include, but are not limited to, synthetic and natural dyes such as titanium dioxide, beta-carotene and extracts of grapefruit peel.

Suitable examples of pharmaceutically acceptable sweeteners for the oral compositions include, but are not limited to, aspartame, saccharin, saccharin sodium, sodium cyclamate, xylitol, mannitol, sorbitol, lactose and sucrose.

Suitable examples of pharmaceutically acceptable buffers include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants include, but are not limited to, sodium lauryl sulfate and polysorbates.

Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

Suitable examples of pharmaceutically acceptable stabilizers and antioxidants include, but are not limited to, ethylenediaminetetraacetic acid (EDTA), thiourea, tocopherol and butyl hydroxyanisole.

The compounds of the invention may also, for example, be formulated as suppositories e.g., containing conventional suppository bases for use in human or veterinary medicine or as pessaries e.g., containing conventional pessary bases.

For percutaneous or mucosal external administration, the compounds of Formula (I) can be prepared in a form of an ointment or cream, gel or lotion. Ointments, creams and gels can be formulated using a water or oil base with addition of an appropriate emulsifier or gelling agent. Formulation of the present compounds is especially significant for respiratory inhalation, wherein the compounds of Formula (I) are to be delivered in the form of an aerosol under pressure. It is preferred to micronize the compounds of Formula (I) after they have been homogenized, e.g., in lactose, glucose, higher fatty acids, sodium salt of dioctylsulfosuccinic acid or, most preferably, in carboxymethyl cellulose, in order to achieve a microparticle size of 5 μm or less for the majority of particles. For the inhalation formulation, the aerosol can be mixed with a gas or a liquid propellant for dispensing the active substance. An inhaler or atomizer or nebulizer may be used. Such devices are known. See, e.g., Newman et al., *Thorax*, 1985, 40:61-676 Berenberg, M., *J. Asthma USA*, 1985, 22:87-92. A Bird nebulizer can also be used. See also U.S. Pat. Nos. 6,402,733; 6,273,086; and 6,228,346.

For application topically to the skin, the agent of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax, sorbitan monostearate, a polyethylene glycol, liquid paraffin, polysorbate 60, cetyl esters wax, cetearyl alcohol, 2-octyldodecanol, benzyl alcohol, and water. Such compositions may also contain other pharmaceutically acceptable excipients, such as polymers, oils, liquid carriers, surfactants, buffers, preservatives, stabilizers, antioxidants, moisturizers, emollients, colorants, and odorants.

Examples of pharmaceutically acceptable polymers suitable for such topical compositions include, but are not limited to, acrylic polymers; cellulose derivatives, such as carboxymethylcellulose sodium, methylcellulose or hydroxypropylcellulose; natural polymers, such as alginates, tragacanth, pectin, xanthan and cytosan.

As indicated, the compound of the present invention can be administered intranasally or by inhalation and is conveniently delivered in the form of a dry powder inhaler or an aerosol spray presentation from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134AT"") or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g., using a mixture of ethanol and the propellant as the solvent, which may additionally contain a lubricant, e.g., sorbitan trioleate.

Capsules and cartridges (made, for example, from gelatin) for use in an inhaler or insufflator may be formulated to contain a powder mix of the compound and a suitable powder base such as lactose or starch.

For topical administration by inhalation the compounds according to the invention may be delivered for use in human or veterinary medicine via a nebulizer.

The pharmaceutical compositions of the invention may contain from 0.01 to 99% weight per volume of the active material.

A therapeutically effective amount of a compound of the present invention can be determined by methods known in the art. Since a compound of the present invention is more efficiently delivered to the desired site than other compounds such as azithromycin and clarithromycin, a lesser amount of a compound of the present invention can be delivered (on a molar basis) compared to the azithromycin or clarithromycin while still achieving the same therapeutic effect. Thus, the table below serves only as a guide. Broad and preferred effective amounts of a compound of the invention or a pharmaceutically acceptable derivative thereof are shown in the table below.

|  | Amount of Compound of Formula (I), or Pharmaceutically Acceptable Derivative Thereof (μmol/kg body weight/day) |
|---|---|
| Broad Range | from about 0.004 to about 4000 |
| Narrower | from about 0.04 to about 400 |
| Still Narrower | from about 4 to about 400 |
| Narrowest | from about 12 to about 120 |

The efficacy of the present compounds can be assessed by any method for assessing inflammation or anti-inflammatory effect. There are many known methods for this purpose including without limitation use of contrast ultrasound in conjunction with injection of microbubbles, measurement of inflammatory cytokines (such as TNF-α, IL-1, IFN-γ) measurement of activated immune system cells (activated T cells, cytotoxic T cells specifically recognizing the inflamed or transplanted tissue) as well as by observation (reduction of oedema, reduction of erythema, reduction of pruritus or burning sensation, reduction of body temperature, improvement in function of the afflicted organ) as well as any of the methods provided below.

Administration may be once a day, twice a day, or more often, and may be decreased during a maintenance phase of the disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art.

Biological Assays

The therapeutic effect of compounds of the present invention was determined in in vitro and in vivo experiments such as the following.

The cytokines assayed in the biological examples, when expressed at elevated amounts, are markers for inflammation and, in the case of cell proliferation, the behaviors of these immune cells are also markers for their activation and, therefore, inflammation. Consequently, reduction of pro-inflammatory cytokine expression or secretion and reduction in cell proliferation is a measure of a compound's anti-inflammatory activity.

A compound analyzed using the biological assays as defined herein is considered to be "active" if it is better than a positive control (i.e., azithromycin) in at least one inhibitory function (i.e., inhibition of TNF-α or IL-6) after stimulation with at least one stimulant (e.g., PMA or PHA). More preferably, an active compound exhibits more than 50% inhibition in at least one inhibitory function Sample Preparation Substances, used in in vitro experiments, were dissolved in dimethyl sulfoxide (DMSO) (Kemika, Croatia) at concentrations of 50 mM and 10 mM and were further diluted to the final concentrations of 50 mM and 10 mM in 1 mL Dulbecco's modified Eagle medium (DMEM) supplemented with 1% heat inactivated fetal bovine serum (FBS), 1% glutamax, 50 U/ml penicillin, 50 μg/ml streptomycin and 2.5 μg/mL Fungizone (amphotericin B). Media and all media supplements were purchased from Gibco, Australia, except FBS that was from Sigma, USA.

Isolation of Peripheral Blood Leukocytes

Peripheral blood leukocytes (PBL) were obtained from venous blood of healthy volunteers by sedimentation on 2% dextran T-500 (Amersham Biosciences, USA) and subsequent centrifugations of leukocyte-rich plasma.

Inhibition of Proinflammatory Cytokine Production by Stimulated Human Peripheral Blood Leukocytes In Vitro Peripheral blood leukocytes (PBL), isolated as described above, were seeded in a 48-well plate at a concentration of 3-5×10$^6$ cell per well in culture medium consisting of RPMI 1640 medium (Institute of Immunology, Croatia) supplemented with 10% heat-inactivated fetal calf serum (FCS, Biowhittaker, USA), 100 U/ml penicillin (Gibco, Australia), 100 μg/ml streptomycin (Gibco, Australia) and 2 mM L-glutamine (Gibco, Australia), and preincubated with the tested compounds for 2 h at 37° C., in an atmosphere of 5% $CO_2$, and 90% humidity. Afterwards, stimuli (Sigma, USA) were added to a final concentration of 2 μg/mL lipopolysaccharide (LPS), 1 μg/mL phorbol 12-myristate 13-acetate (PMA) or 120 μg/mL zymosan. Samples were incubated overnight under conditions described above. At the end of incubation supernatants were transferred to eppendorf tubes and centrifuged for 10 min at 1500 g. Concentrations of human TNF-α, IL-1β, IL-6 and IL-8 were determined in cell supernatants by sandwich ELISA, using capture and detection antibodies (R&D, USA) according to manufacturer's recommendations.

Inhibition (as percentage) was calculated using the following formula:

% inhibition=(1−concentration of cytokines in sample/concentration of cytokines in positive control)×100 where "positive control" refers to stimulated samples not treated with substances.

TABLE 1

Percentage of inhibition of proinflammatory cytokine production by stimulated PBL treated with compounds

| | | TNF-α | | | IL-1β | | | IL-6 | | | IL-8 | | |
|---|---|---|---|---|---|---|---|---|---|---|---|---|---|
| | | LPS | PMA | zymosan | LPS | PMA | zymosan | LPS | PMA | zymosan | LPS | PMA | zymosan |
| azithromycin | 10 μM | 36 | 0 | 6 | 28 | 0 | 20 | 15 | 0 | 20 | 0 | 0 | 0 |
| | 50 μM | 20 | 0 | 64 | 48 | 0 | 75 | 40 | 0 | 75 | 0 | 0 | 0 |
| clarithromycin | 10 μM | 0 | 0 | 0 | 0 | 26 | 36 | 11 | 0 | 28 | 23 | 33 | 0 |
| | 50 μM | 0 | 0 | 0 | 0 | 33 | 59 | 0 | 0 | 0 | 0 | 0 | 0 |
| Example 2 | 10 μM | 37 | 34 | 13 | 83 | 60 | 96 | 40 | 17 | 45 | 40 | 0 | 32 |
| | 50 μM | 80 | 55 | 60 | 91 | 78 | 94 | 94 | 68 | 91 | 96 | 92 | 87 |
| Example 4 | 10 μM | 0 | 69 | 0 | 75 | 97 | 61 | 37 | 96 | 55 | 29 | 55 | 10 |
| | 50 μM | 100 | 100 | 100 | 100 | 100 | 100 | 100 | 100 | 100 | 100 | 90 | 100 |
| Example 5 | 10 μM | 3 | 29 | 17 | 75 | 91 | 68 | 38 | 78 | 51 | 22 | 48 | 48 |
| | 50 μM | 92 | 100 | 100 | 80 | 100 | 100 | 100 | 100 | 100 | 95 | 83 | 100 |
| Example 10 | 10 μM | 6 | 68 | 10 | 70 | 80 | 78 | 35 | 69 | 40 | 13 | 23 | 6 |
| | 50 μM | 65 | 78 | 75 | 88 | 94 | 100 | 92 | 92 | 100 | 77 | 76 | 82 |
| Example 12 | 10 μM | 22 | 30 | 33 | 50 | 54 | 29 | 9 | 43 | 0 | 16 | 31 | 20 |
| | 50 μM | 0 | 75 | 0 | 71 | 92 | 72 | 19 | 93 | 96 | 51 | 27 | 52 |
| Example 18 | 10 μM | 7 | 50 | 12 | 44 | 66 | 32 | 9 | 53 | 18 | 1 | 16 | 3 |
| | 50 μM | 0 | 82 | 0 | 73 | 87 | 76 | 50 | 47 | 47 | 30 | 13 | 21 |
| Example 19 | 10 μM | 11 | 53 | 18 | 44 | 66 | 35 | 16 | 56 | 19 | 6 | 14 | 9 |
| | 50 μM | 7 | 82 | 12 | 73 | 86 | 80 | 56 | 61 | 44 | 32 | 0 | 26 |
| Example 23 | 10 μM | 0 | 58 | 0 | 73 | 81 | 70 | 8 | 51 | 26 | 0 | 0 | 0 |
| | 50 μM | 97 | 79 | 96 | 100 | 98 | 100 | 100 | 92 | 100 | 95 | 90 | 98 |
| Example 24 | 10 μM | 0 | 65 | 0 | 65 | 84 | 70 | 8 | 48 | 33 | 0 | 3 | 0 |
| | 50 μM | 91 | 68 | 92 | 98 | 98 | 100 | 98 | 89 | 100 | 94 | 81 | 92 |

Isolation of Peripheral Blood Mononuclear Cells

Heparinized peripheral blood was obtained from healthy donors, and peripheral blood mononuclear cells (PBMC) were isolated by Histopaque 1077 (Sigma, USA) density centrifugation at 400 g for 30 minutes. Collected PBMC were centrifuged in plasma at 400 g/10 min, resuspended and washed in RPMI 1640 (Institute of Immunology, Croatia) by centrifugation.

Effects on Human Peripheral Blood Mononuclear Cell Proliferation In Vitro

Influence of substances at two different concentrations (50 μM and 10 μM) on proliferation of human peripheral blood mononuclear cells (PBMC) was assessed.

Heparinized peripheral blood was obtained from healthy donors, and PBMC were isolated by Histopaque 1077 (Sigma, USA) density centrifugation at 400 g for 30 minutes. 5×10$^4$ cells/well were cultured for 3 days in the RPMI medium as described above, in the presence (positive control) or absence (negative control) of stimulators [PHA (2.5 μg/mL) (Sigma, USA) or both PMA (10 ng/mL) (Sigma, USA) and ionomycin (500 ng/mL) (Calbiochem, USA)] and tested substances at 37° C. in 5% $CO_2$ and 90% humidity. The cells were pulsed with 1 μCi of ($^3$H)thymidine (Amersham, USA) per well during the last 18 h of the cultures and were harvested on a 96-well filter (Packard Bioscience, USA) with a multiple cell harvester (Packard, USA). The incorporation of ($^3$H)thymidine in activated cells was measured by Top-Count NXT (Packard, USA).

Inhibition of cell proliferation (as a percentage) was calculated using the following formula:

% inhibition=(1−($^3$H)thymidine incorporation expressed in counts per minute (cpm) in sample/ (3H)thymidine incorporation expressed in cpm in positive control)×100 where "positive control" refers to stimulated samples not treated with substances.

TABLE 2

Percentage of inhibition of proliferation of stimulated PBMC treated with compounds

|  |  | PBMC | |
| --- | --- | --- | --- |
|  |  | PHA | PMA + ionomycin |
| azithromycin | 10 μM | 5 | 9 |
|  | 50 μM | 29 | 31 |
| clarithromycin | 10 μM | 0 | 9 |
|  | 50 μM | 7 | 14 |
| Example 2 | 10 μM | 80 | 0 |
|  | 50 μM | 98 | 99 |
| Example 5 | 10 μM | 99 | 90 |
|  | 50 μM | 100 | 100 |

Cytotoxicity Assay on THP-1, Hep G2 and A549 Cell Lines

Anti-inflammatory activity of compounds, i.e. observed inhibition of cytokine production and inhibition of proliferation in vitro, is not a consequence of their cytotoxicity.

Measurement of the succinate dehydrogenase activity in living cells was performed in order to assess the cytotoxicity of compounds of the invention. Cells were cultured for 24 hours in RPMI medium as described above at 37° C., in the presence of the tested compounds at concentrations of 50 μM and 12.5 μM. Afterwards, MTT [3-(4,5-dimethylthiazole-2-yl)-2,5-diphenyl tetrazolium bromide] (Promega, USA) as detection reagent was added and incubated for 0.5-2 hours. The amount of produced MTT-Formazan was determined spectrophotometrically at 490 nm (Mosmann, J. Immunol. Methods, 1983, 65: 55-63).

Percentage of viable cells was calculated using the following formula:

% viable cells=(1−OD$_{490}$ treated cells/OD$_{490}$ non-treated cells)×100

TABLE 3

Percentage of viable cells after treatment with substances

|  |  | THP-1 | A549 | Hep G2 |
| --- | --- | --- | --- | --- |
| azithromycin | 12.5 μM | 100 | 100 | 100 |
|  | 50 μM | >95 | 100 | >95 |
| clarithromycin | 12.5 μM | 100 | 100 | 100 |
|  | 50 μM | >95 | 100 | 100 |
| Example 2 | 12.5 μM | >85 | >90 | 100 |
|  | 50 μM | >95 | >90 | 100 |
| Example 4 | 12.5 μM | 100 | >95 | >85 |
|  | 50 μM | 100 | >95 | >95 |
| Example 5 | 12.5 μM | 100 | 100 | >86 |
|  | 50 μM | >80 | 100 | 100 |
| Example 10 | 12.5 μM | 100 | >80 | 100 |
|  | 50 μM | 100 | >90 | 100 |
| Example 12 | 12.5 μM | >90 | >90 | >95 |
|  | 50 μM | 100 | >90 | >90 |
| Example 18 | 12.5 μM | 100 | 100 | >95 |
|  | 50 μM | 100 | 100 | 100 |
| Example 19 | 12.5 μM | 100 | 100 | 100 |
|  | 50 μM | 100 | >95 | 100 |

TABLE 3-continued

Percentage of viable cells after treatment with substances

|  |  | THP-1 | A549 | Hep G2 |
| --- | --- | --- | --- | --- |
| Example 23 | 12.5 μM | 100 | 100 | 100 |
|  | 50 μM | 100 | >95 | 100 |
| Example 24 | 12.5 μM | 100 | >90 | >95 |
|  | 50 μM | 100 | >90 | 100 |

In all the tests, the compounds of the present invention were found to be very active as anti-inflammatories, and the anti-inflammatory activity was found to be comparable or greater than that of the comparative compounds azithromycin and clarithromycin.

It is therefore clear that the compounds of Formula (I), which have anti-inflammatory activity, can be useful in both acute and chronic treatment and in the prophylaxis of inflammatory pathologies, especially of those pathologies associated with altered cellular functionality of the neutrophils, for example rheumatoid arthritis, vasculitis, glomerulonephritis, damage from ischemic reperfusion, atherosclerosis, septic shock, ARDS, COPD, cystic fibrosis and asthma.

The therapeutically effective quantities will depend on the age and on the general physiological condition of the patient, the route of administration and the pharmaceutical formulation used. The therapeutic doses will generally be between about 10 and 2000 mg/day and preferably between about 30 and 1500 mg/day.

The compounds of the present invention for use in treatment and/or prophylaxis of the pathologies indicated above will preferably be used in a pharmaceutical form suitable for oral, rectal, sublingual, parenteral, topical, transdermal or inhalational administration.

The present invention further relates to pharmaceutical formulations containing a therapeutically effective quantity of a compound of Formula (I) or one of its salts or derivatives mixed with a pharmaceutically acceptable vehicle. The pharmaceutical formulations of the present invention can be liquids that are suitable for oral and/or parenteral administration, for example, drops, syrups, solutions, injectable solutions that are ready for use or are prepared by the dilution of a freeze-dried product, but are preferably in a solid or semisolid form such as tablets, capsules, granules, powders, pellets, pessaries, suppositories, creams, salves, gels, ointments; or solutions, suspensions, emulsions, or other forms suitable for administration by the transdermal route or by inhalation.

Depending on the type of formulation, in addition to a therapeutically effective quantity of one or more compounds of Formula (I), they will contain solid or liquid excipients or diluents for pharmaceutical use and possibly other additives normally used in the preparation of pharmaceutical formulations, such as thickeners, aggregating agents, lubricants, disintegrating agents, flavorings and colorants.

The pharmaceutical formulations of the invention can be produced in accordance with the usual methods.

The following examples are provided for better illustration of the present invention. In the following examples, the structural representation of a pendant —O or —N is equivalent to the —OH, —NH, or —NH$_2$ as appropriate based on atom valency.

The following abbreviations are used in the text: DBU for 1,8-diazabicyclo[5.4.0]undec-7-ene, DCM for dichloromethane, DMAP for 4-dimethylaminopyridine, DMF for N,N-dimethylformamide, DMSO for dimethyl sulfoxide, EDCxHCl for 1-(3-dimethylaminopropyl)-3-ethylcarbodiimide hydrochloride, EtOAc for ethyl acetate, HOAc for acetic acid, MeOH for methanol, EtOH for ethanol, t-BuOH for tert-butanol, TEA for triethylamine, DEA for diethylamine, THF for tetrahydrofuran, DCC for dicyclohexylcarbodiimide, DIPEA for N,N-diisopropylethylamine.

The compounds in the following examples preferably have the substituent bonded at the C-2 of the desosaminyl sugar in the S absolute stereochemical configuration, and therefore, is in an anti stereochemical configuration compared to the stereochemical configurations of the substituents bonded at the C-1 and C-3 of the desosaminyl sugar.

The compounds and processes of the present invention will be better understood in connection with the following examples, which are intended as an illustration only and not limiting the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

EXAMPLES

2'-O-Acetyl-protected compounds may be prepared by the procedure described by W. R. Baker et al. in *J. Org. Chem.* 1988, 53, 2340. 9-O-(2-chlorobenzyl)-protected oxime compounds may be prepared by the procedure described by Y. Watanabe et al. in *J. Antibiot.* 1993, 46, 1163. 9-O-(1-isopropoxycyclohexyl)-protected oxime compounds may be prepared by the procedure described by Z. Ma et al. in *J. Med. Chem.* 2001, 44, 4137. 11,12-Carbonate compounds may be prepared by procedures as described in international patent application WO 02/50091 or by procedures as described by S. Djokic et al. in *J. Chem. Res.* (S) 1988, 152. 11-O-Methyl azithromycin may be prepared by procedures as described by Kobrehel et al. in *J. Antibiotics* 1992, 45, 527. 3-O-Decladinosyl compounds may be prepared as described by Lazarevski et al. international patent application WO 99/51616. 11,12-Cyclic carbamate compounds may be prepared by procedures as described in U.S. Pat. No. 6,262,030.

Example 1

3-O-Propenoyl-3-O-decladinosyl-6-O-methyl-9a-aza-9a-homoerythromycin A

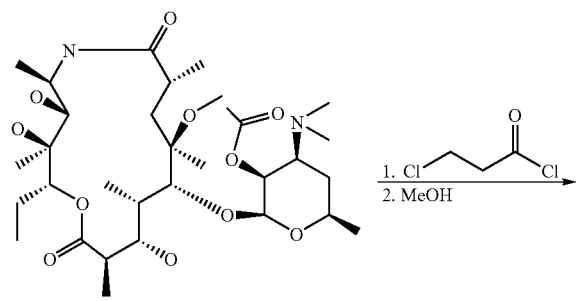

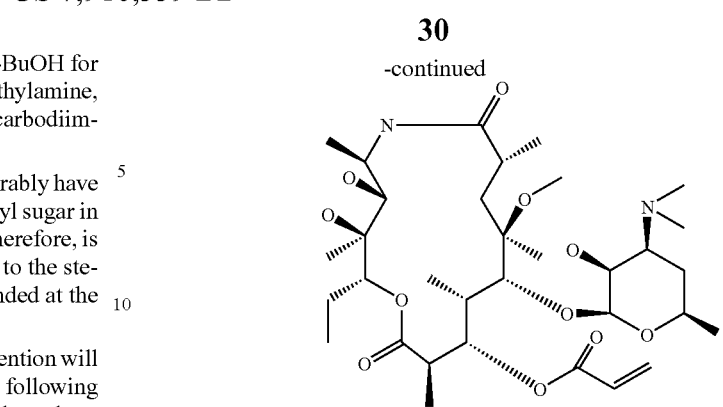

To a solution of the compound obtained according to WO 99/51616, Example 6 (1.3 g, 2.01 mmol) in dry toluene (10 ml) were added TEA (1.14 ml, 8.24 mmol) and 3-chloropropionyl chloride (0.3 ml, 3.15 mmol). The reaction mixture was stirred for 15 minutes at room temperature. The toluene layer was washed with $NaHCO_3$ and brine, and evaporated under vacuum giving a crude residue (0.56 g). The residue was dissolved in methanol (30 ml) and stirred for 48 hours at room temperature.

Methanol was evaporated under reduced pressure and the crude product was purified by flash chromatography (DCM/MeOH/$NH_4OH$=90:9:1.5) to afford the title compound (0.51 g).

MS (ES+) m/z: $[MH]^+$=659.4

Example 2

3-O-(3-Diethylamino-propionyl)-3-O-decladinosyl-6-O-methyl-9a-aza-9a-homoerythromycin A

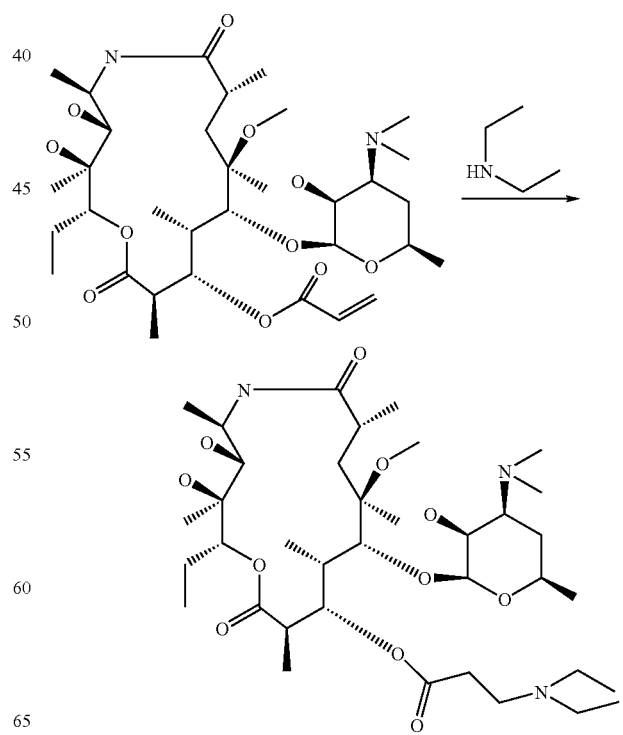

Diethyl amine (0.24 ml, 2.30 mmol) was added to a solution of the compound made in Example 1 (0.25 g, 0.38 mmol) in dry methanol (30 ml) and the reaction mixture was stirred for 20 hours at 40° C. An additional amount of diethyl amine was added (0.08 ml, 0.77 mmol) and the mixture was further stirred for 1 hour. Methanol was evaporated under reduced pressure and the crude product was purified by flash chromatography (DCM/MeOH/NH$_4$OH=90:9:0.5) to afford the title compound (0.14 g).

MS (ES+) m/z: [MH]$^+$=732.62

$^{13}$C-NMR (125 MHz, CDCl$_3$) δ: 178.0, 177.1, 172.2, 103.4, 81.1, 797, 79.7, 77.5, 74.0, 73.9, 70.4, 69.5, 65.9, 50.8, 48.2, 46.7 (×2), 45.8, 42.7, 40.6, 40.4, 36.6, 33.6, 32.8, 28.9, 21.2, 20.9, 19.2, 18.1, 16.2, 16.0, 15.0, 11.3 (×2), 9.1

Example 3

2'-O-Acetyl-3-O-propenoyl-3-O-decladinosyl-6-O-methyl-erythromycin A

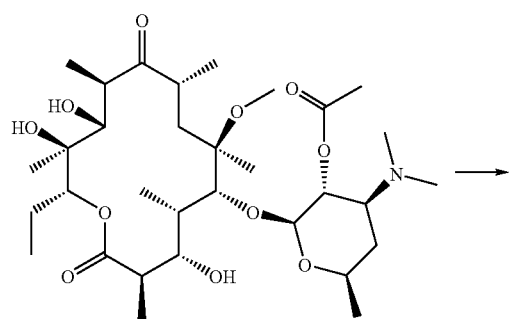

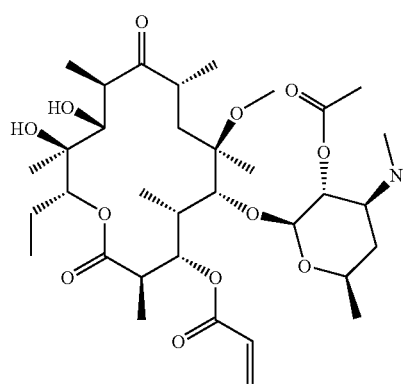

To a solution of 2'-O-acetyl-3-O-decladinosyl-6-O-methyl erythromycin A (0.63 g, 1.0 mmol) in toluene (15 ml), TEA (0.42 ml, 3.0 mmol) and 3-chloropropionyl chloride (0.095 ml, 1.0 mmol) were added. The reaction mixture was stirred at room temperature for 15 minutes and an additional portion of TEA (0.42 ml, 3.0 mmol) and 3-chloropropionyl chloride (0.095 ml, 1.0 mmol) were added. After an additional 15 minutes of stirring, toluene (15 ml) was added and the solution washed with a saturated aqueous solution of NaHCO$_3$ and brine, and dried over anhydrous Na$_2$SO$_4$. Evaporation of the solvent afforded crude product which was purified using column chromatography on silica gel (DCM/MeOH/NH$_4$OH=90:5:0.5 as eluent) to give the title product (0.41 g).

Example 4

3-O-Propenoyl-3-O-decladinosyl-6-O-methyl-erythromycin A

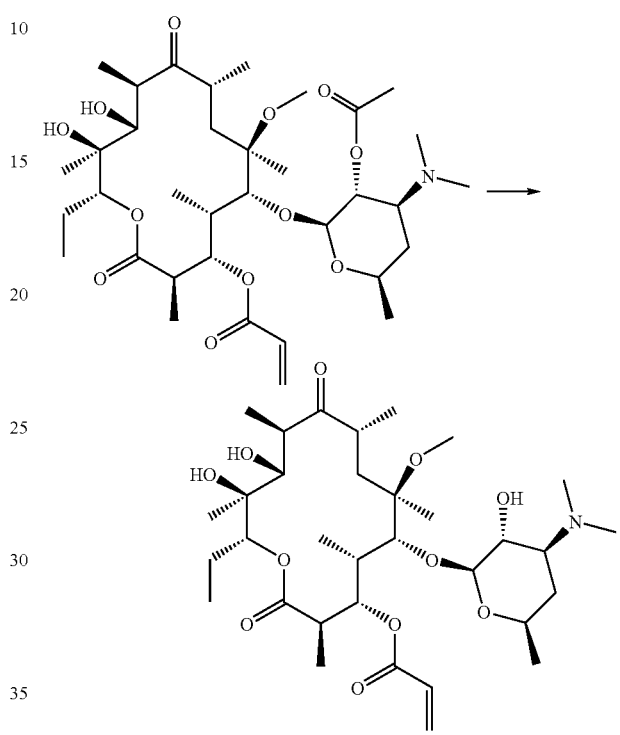

A solution of the compound made in Example 3 (0.686 g, 1.0 mmol) in MeOH (150 ml) was stirred at 40° C. for 18 hours, MeOH was evaporated and the crude product purified using column chromatography on silica gel (DCM/MeOH/NH$_4$OH=90:9:1.5 as eluent) to give the title product (0.51 g).

MS (ES+) m/z: [MH]$^+$=644.3

Example 5

3-O-(3-Diethylamino-propionyl)-3-O-decladinosyl-6-O-methyl-erythromycin A

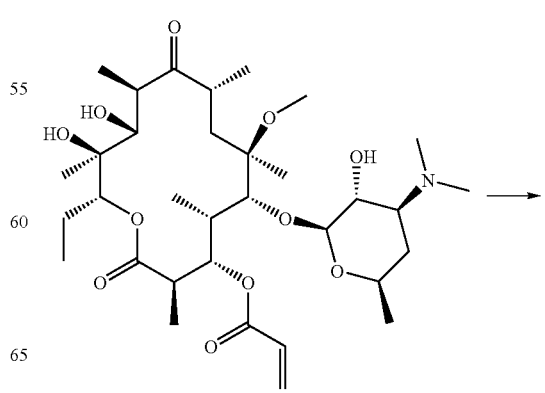

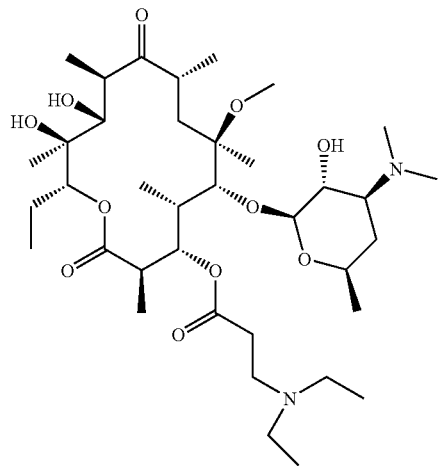

To a solution of the compound made in Example 4 (0.686 g, 1.0 mmol) in dry MeOH (30 ml), diethylamine (1.04 ml, 10.0 mmol) was added. The reaction mixture was stirred at 40° C. for 20 hours, methanol was evaporated and the crude product purified using column chromatography on silica gel (DCM/MeOH/NH$_4$OH=90:9:0.5 as eluent) to afford the title product (0.43 g).

MS (ES+) m/z: [MH]$^+$=717.4.

Example 6

2'-O-Acetyl-6-O-methyl-3-O-propenoyl-3-O-decladinosyl-erythromycin A 11,12-cyclic carbamate Intermediate: 2'-O-Acetyl-6-O-methyl-3-O-decladinosyl-erythromycin A 11,12-cyclic carbamate

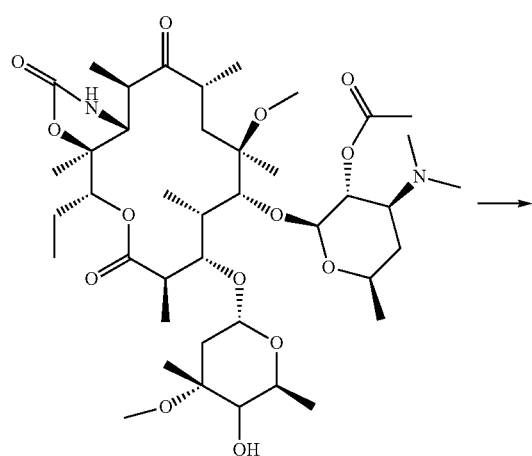

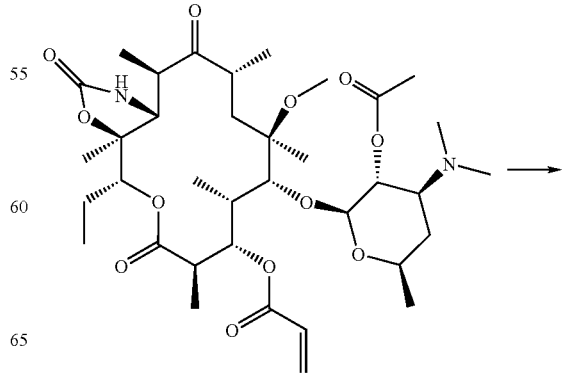

A solution of 2'-O-acetyl-6-O-methyl-erythromycin A 11,12-cyclic carbamate (0.82 g, 1.0 mmol) in 0.25 N HCl (15 ml) was stirred overnight at room temperature and extracted with DCM (3×15 ml). The pH of the water layer was adjusted to 9 and extracted with EtOAc (4×15 ml). The organic layer was washed with water (1×50 ml), and dried over K$_2$CO$_3$ and solvent was evaporated to afford the Intermediate (0.58 g).

2'-O-Acetyl-6-O-methyl-3-O-propenoyl-3-O-decladinosyl-erythromycin A 11,12-cyclic carbamate Starting from the Intermediate of Example 6 (0.657 g, 1.0 mmol), the title compound was made according to the procedure of Example 3. The crude compound was obtained and purified by column chromatography on silica gel (EtOAc/hexane/TEA=6:3:2 as eluent) to give the title compound (0.533 g).

MS (ES+) m/z: [MH]$^+$=711.1.

Example 7

6-O-Methyl-3-O-propenoyl-3-O-decladinosyl-erythromycin A 11,12-cyclic carbamate

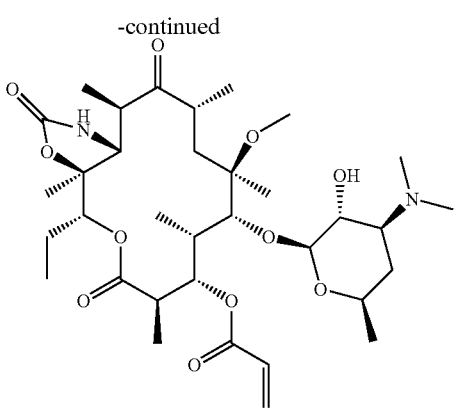

Starting from the final compound synthesized in Example 6 (0.711 g, 1.0 mmol), the title compound was made according to the procedure of Example 4 (0.615 g).
MS (ES+) m/z: $[MH]^+=669.1$.

Example 8

6-A-Methyl-3-O-(3-diethylamino-propionyl)-3-O-decladinosyl-erythromycin A 11,12-cyclic carbamate

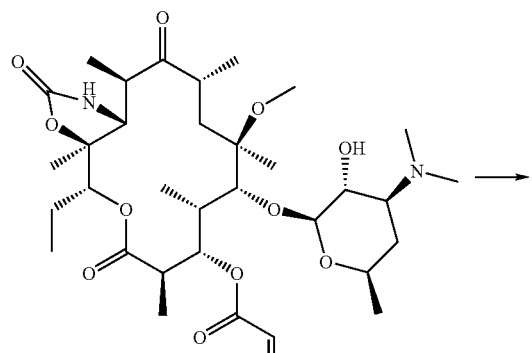

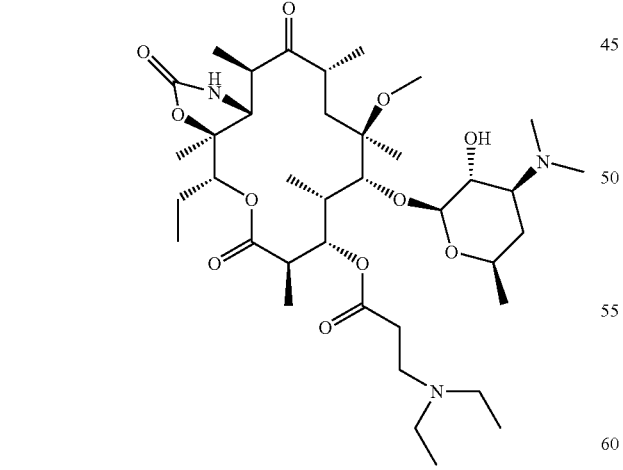

To a solution of the compound synthesized in Example 7 (0.669 g, 1.0 mmol) in dry methanol (30 ml), diethylamine (1.04 ml, 10.0 mmol) was added. The reaction mixture was stirred at 55° C. for 48 hours, methanol was evaporated and the crude product was purified using column chromatography on silica gel (DCM/MeOH/NH$_4$OH=90:9:0.5 as eluent) to afford the title product (0.586 g).
MS (ES+) m/z: $[MH]^+=742.5$ Example 9

3-O-Propenoyl-3-O-decladinosyl-3'-N-demethyl-6-O-methyl-9a-aza-9a-homoerythromycin A

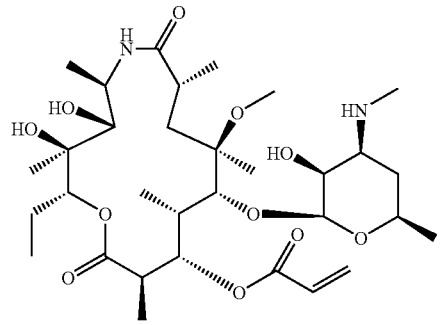

To a stirred solution of the compound synthesized in Example 1 (0.5 g, 0.76 mmol) and NaOAc trihydrate (0.185 g, 2.2 mmol) in methanol (12.5 ml), solid iodine (0.195 g, 0.77 mmol) was added. The reaction mixture was irradiated with 500 W halogen lamp for 3 hours, cooled to room temperature, and the solvent was evaporated. The solid residue was dissolved in EtOAc (100 ml), filtered, and the filtrate was washed with saturated aqueous NaHCO$_3$ (25 ml) and brine (25 ml). The organic layer was dried over Na$_2$SO$_4$ and evaporated to give the title compound (0.49 g).
MS (ES+) m/z: $[MH]^+=645.5$ Example 10

3-O-(3-Diethylamino-propionyl)-3-O-decladinosyl-3'-N-demethyl-6-O-methyl-9a-aza-9a-homoerythromycin A

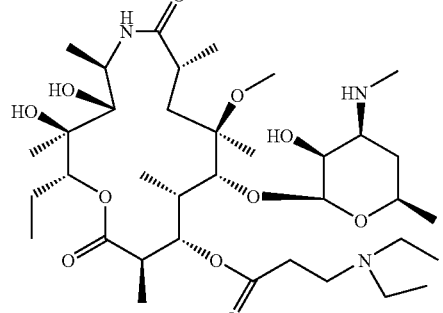

A solution of the compound formed in Example 9 (0.21 g, 0.33 mmol) in diethylamine (5 ml) was stirred overnight at 40° C. Diethylamine was evaporated and the crude product was purified using column chromatography on silica gel (EtOAc/hexane/TEA=10:5:2 as eluent) to afford the title product (0.12 g).

MS (ES+) m/z: [MH]⁺=718.3

Example 11

3-O-Propenoyl-3-O-decladinosyl-azithromycin

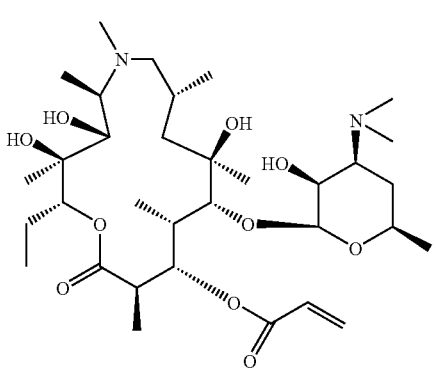

To a solution of 2'-O-acetyl-3-O-decladinosyl azithromycin (1.0 g, 1.6 mmol) and TEA (0.25 ml, 1.8 mmol) in DCM (5 ml), acryloyl chloride (0.4 ml, 4.0 mmol) was added portionwise during 4 hours. The solvent was evaporated and methanol (20 ml) was added. The reaction mixture was stirred at room temperature for 3 days, the solvent was evaporated and the crude product was purified using column chromatography on silica gel (EtOAc/hexane/TEA=10:5:2 as eluent) to give the title product (0.82 g).

MS (ES+) m/z: [MH]⁺=645.4

Example 12

3-O-(3-Diethylamino-propionyl)-3-O-decladinosyl-azithromycin

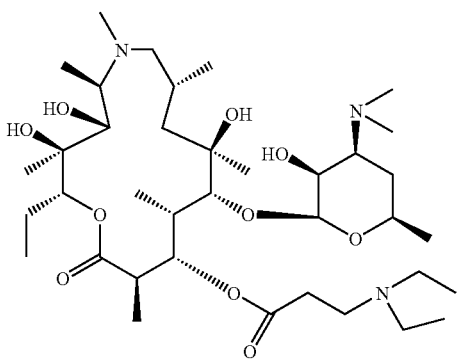

A solution of the compound formed in Example 11 (0.18 g, 0.28 mmol) in DEA (10 ml) was stirred overnight at 40° C.

DEA was evaporated and the crude product was purified using column chromatography on silica gel (EtOAc/hexane/TEA=10:5:2 as eluent) to afford the title product (0.09 g).

MS (ES+) m/z: [MH]⁺=718.3

Example 13

3-O-(2-Diethylamino-acetyl)-3-O-decladinosyl-azithromycin

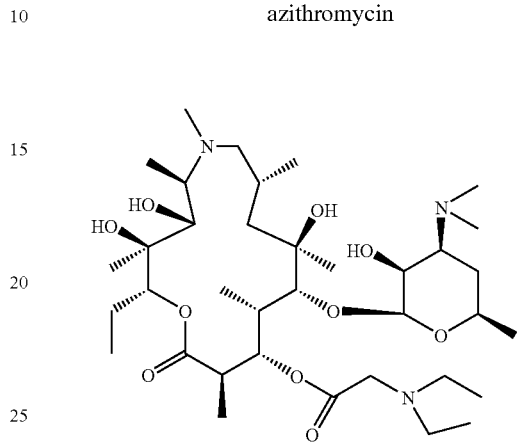

A solution of 2'-O-acetyl-3-O-decladinosyl-azithromycin (0.25 g, 0.4 mmol), diethylaminoacetic acid (0.26 g, 2.0 mmol), EDC×HCl (0.4 g, 2.0 mmol), and DMAP (0.25 g, 2.0 mmol) DCM (5 ml) was stirred overnight at room temperature. Solvent was evaporated, and the residue was dissolved in MeOH (25 ml) and stirred overnight at 40° C. The MeOH was evaporated to afford the title product (0.24 g).

MS m/z: (ES): MH⁺=704.4

Example 14

3-O-(2-Diethylamino-acetyl)-3-O-decladinosyl-6-O-methyl-9a-aza-9a-homoerythromycin A

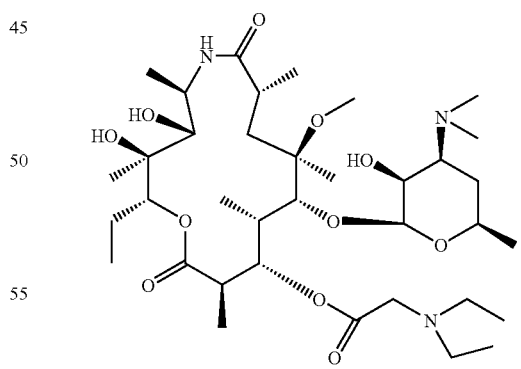

A solution of 2'-O-acetyl-6-O-methyl-3-O-decladinosyl-9a-aza-9a-homoerythromycin A (0.25 g, 0.39 mmol), diethylaminoacetic acid (0.26 g, 2.0 mmol), EDC×HCl (0.4 g, 2.0 mmol), and DMAP (0.25 g, 2.0 mmol) in DCM (5 ml) was stirred overnight at room temperature. Solvent was then evaporated, and the residue was dissolved in MeOH (25 ml) and stirred overnight at 40° C. The solvent was evaporated and the crude product purified using Flashmaster II—solid phase extraction technique (SPE 20 g, DCM/MeOH/NH₄OH=90:5:0.5 as eluent) to afford the title product (0.04 g).

MS m/z: (ES): MH⁺=718.3

Example 15

2'-O-Acetyl-6-O-methyl-3-O-decladinosyl-3-O-(3-aminopropyl)-9a-aza-9a-homoerythromycin A 11,12-cyclic carbonate Intermediate: 2'-O-Acetyl-6-O-methyl-3-O-decladinosyl-3-O-(2-cyanoethyl)-9a-aza-9a-homoerythromycin A 11,12-cyclic carbonate

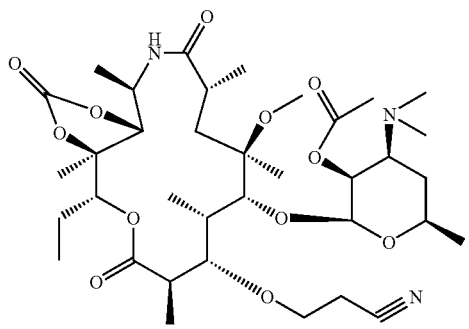

A solution of 2'-O-acetyl-6-O-methyl-3-O-decladinosyl-9a-aza-9a-homoerythromycin A 11,12-cyclic carbonate (0.38 g, 0.56 mmol), t-BuOH (0.13 ml, 1.24 mmol), and NaH (20 mg, 0.5 mmol) in acrylonitrile (9 ml) was stirred for 4 hours at 0° C. and then allowed to warm up to room temperature. Acrylonitrile was evaporated, the residue was dissolved in EtOAc, and the solution was filtered. The filtrate was washed with a saturated aqueous solution of NaHCO₃ (3×20 ml) and brine (3×20 ml) and dried over anhydrous Na₂SO₄. Evaporation of solvent afforded the title product (0.4 g).

MS (ES+) m/z: [MH]⁺=726.6

2'-O-Acetyl-6-O-methyl-3-O-decladinosyl-3-O-(3-aminopropyl)-9a-aza-9a-homoerithromycin A 11,12-cyclic carbonate

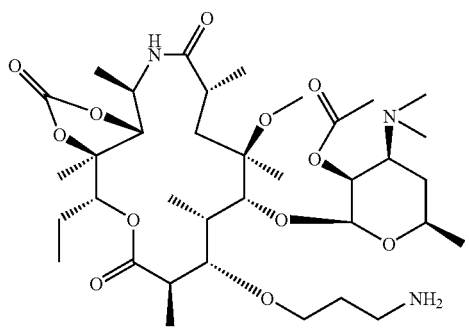

A suspension of the Intermediate formed in Example 15 (0.4 g, 0.55 mmol) and PtO₂ (70 mg) in glacial HOAc (13 ml) was hydrogenated overnight at 4.5 bar. The reaction mixture was filtered, and HOAc was evaporated. The residue was dissolved in DCM (50 ml), H₂O (30 ml) was added, and the pH was adjusted to 9.4. The water layer was extracted with DCM (2×30 ml) and combined organic extracts were dried over anhydrous Na₂SO₄. Evaporation of solvent afforded the title product (0.2 g).

MS (ES+) m/z: [MH]⁺=730.4

Example 16

6-O-Methyl-3-O-decladinosyl-3-O-(3-aminopropyl)-9a-aza-9a-homoerithromycin A

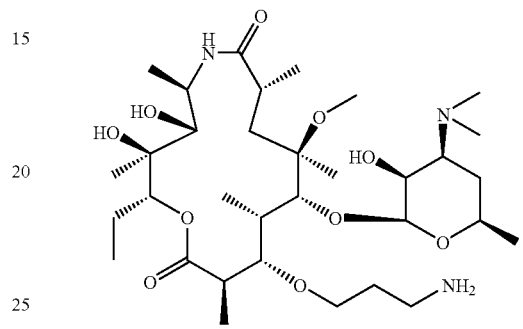

A solution of the final compound synthesized in Example 15 (0.2 g, 0.27 mmol) and K₂CO₃ (0.07 g, 5.1 mmol) in MeOH (10 ml) and H₂O (3 ml) was stirred overnight at 40° C. Methanol was evaporated, and DCM (20 ml) and a saturated aqueous solution of NaHCO₃ (20 ml) were added. Layers were separated and the water layer was extracted with DCM (2×30 ml). Combined organic layers were dried over anhydrous Na₂SO₄. Evaporation of the solvent afforded the title product (0.1 g).

MS (ES+) m/z: [MH]⁺=662.4

Example 17

6-O-Methyl-3-O-decladinosyl-3-O-(3-Diethylaminopropyl)-9a-aza-9a-homoerithromycin A

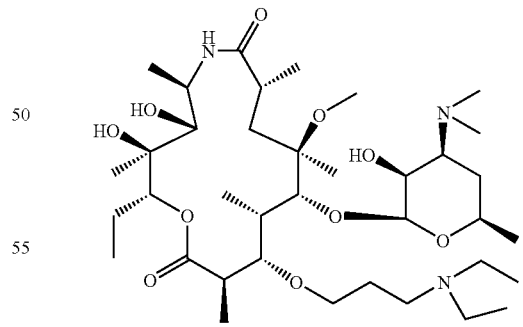

A solution of the compound formed in Example 16 (0.1 g, 0.15 mmol), acetaldehyde (21 μl, 0.37 mmol), NaBH(OAc)₃ (0.077 g (0.37 mmol), and ZnCl₂ (30 mg, 0.22 mmol) in dichlorethane (5 ml) was stirred at room temperature for 3 hours. The reaction mixture was filtered, and dichloroethane was evaporated. To the residue DCM (20 ml) and H₂O (20 ml) were added, the pH was adjusted to 9.3, and the solution was extracted with DCM (2×15 ml). Combined organic layers were dried over anhydrous Na$_2$SO$_4$. Evaporation of solvent afforded the title product (0.03 g).
MS (ES+) m/z: [MH]$^+$=718.3

Examples 18 to 26

General Procedure

To a solution of the compound formed in Example 1 in acetonitrile (5 ml), the corresponding amine compound (3 equivalents) was added. The mixture was heated at 60° C. for 48 hours. The solvent was evaporated under reduced pressure and the crude product purified by column chromatography (DCM/MeOH/NH$_4$OH=90:9:0.5) to afford the desired product.

The table that follows gives the structures of the amine compounds added, as well as the final products of Formula (I).

| Amine | Product | MS (ES+) m/z [MH]$^+$ |
|---|---|---|
| 1-(2-diethylaminoethyl)-piperazine | Example 18<br>6-O-Methyl-3-O-decladinosyl-3-O-{3-[4-(2-Diethylamino-ethyl)-piperazin-1-yl]-propionyl}-9a-aza-9a-homoerythromycin A | 844.3 |
| 1-(2-dimethylaminoethyl)-piperazine | Example 19<br>6-O-Methyl-3-O-decladinosyl-3-O-{3-[4-(2-Dimethylamino-ethyl)-piperazin-1-yl]-propionyl}-9a-aza-9a-homoerythromycin A | 816.2 |

| Amine | Product | MS (ES+) m/z [MH]+ |
|---|---|---|
| | | 761.2 |
| 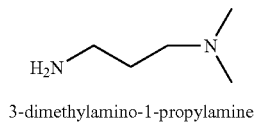 3-dimethylamino-1-propylamine | 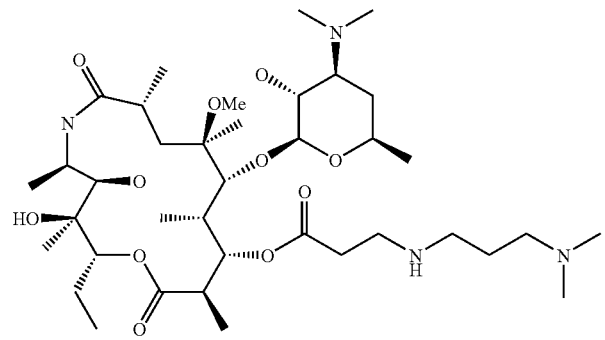 Example 20 6-O-Methyl-3-O-decladinosyl-3-O-[3-(3-Dimethylamino-propylamino)-propionyl]-9a-aza-9a-homoerythromycin A | |
| | | 747.2 |
| 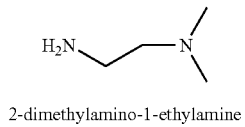 2-dimethylamino-1-ethylamine | 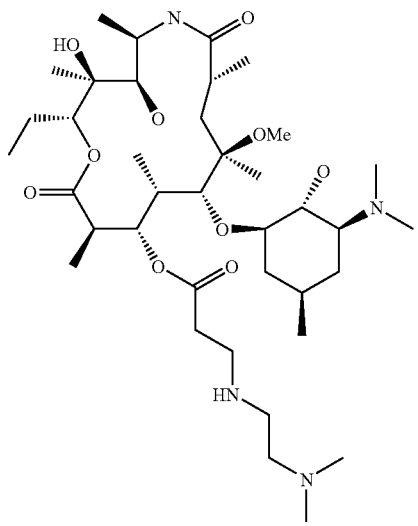 Example 21 6-O-Methyl-3-O-decladinosyl-3-O-[3-(2-Dimethylamino-ethylamino)-propionyl]-9a-aza-9a-homoerythromycin A | |

-continued

| Amine | Product | MS (ES+) m/z [MH]+ |
|---|---|---|
| 1-(3-diethylaminopropyl)-piperazine | Example 22<br>6-O-Methyl-3-O-decladinosyl-3-O-{3-[4-(3-Diethylamino-propyl)-piperazin-1-yl]-propionyl}-9a-aza-9a-homoerythromycin A | 858.4 |
| 2-(methylamino)-ethanol | Example 23<br>6-O-Methyl-3-O-decladinosyl-3-O-{3-[(2-Hydroxy-ethyl)-methyl-amino]-propionyl}-9a-aza-9a-homoerythromycin A | 734.2 |

-continued
| Amine | Product | MS (ES+) m/z [MH]+ |
|---|---|---|
| | | 870.3 |
| 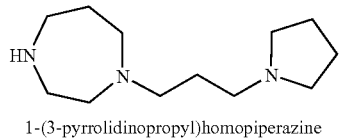 1-(3-pyrrolidinopropyl)homopiperazine | 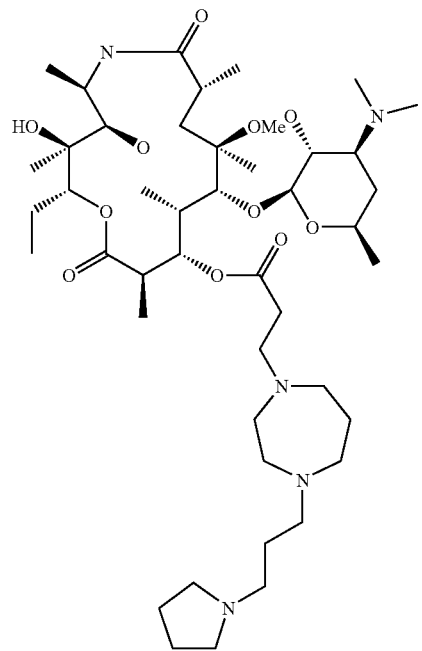 Example 24 6-O-Methyl-3-O-decladinosyl-3-O{3-[4-(3-Pyrrolidin-1-yl-propyl)-[1,4]diazepan-1-yl]-propionyl}-9a-aza-9a-homoerythromycin A | |
| | | 789.3 |
| 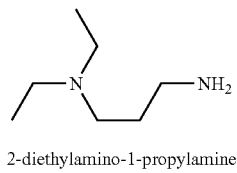 2-diethylamino-1-propylamine | 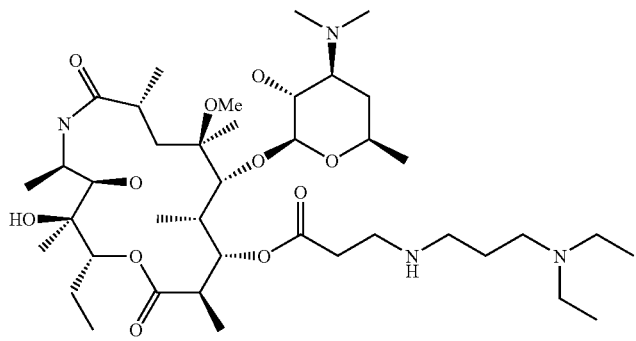 Example 25 6-O-Methyl-3-O-decladinosyl-3-O-[3-(3-Diethylamino-propylamino)-propionyl]-9a-aza-9a-homoerythromycin A | |

-continued

| Amine | Product | MS (ES+) m/z [MH]+ |
|---|---|---|
| 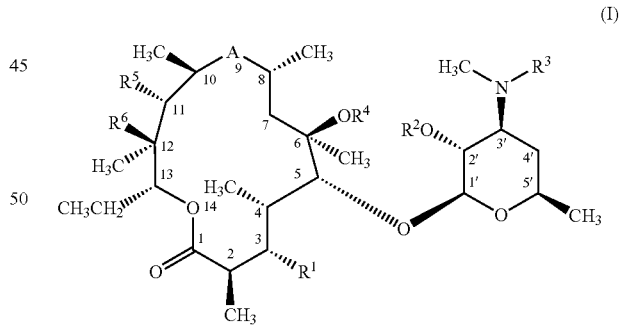 2-diethylamino-1-ethylamine | Example 26 6-O-Methyl-3-O-decladinosyl-3-O-[3-(2-Diethylamino-ethylamino)-propionyl]-9a-aza-9a-homoerythromycin A | 775.0 |

Example 27
3-O-(3-Diethylamino-propionyl)-3-O-decladinosyl-6-O-methyl-9-deoxo-9-dihydro-9-hydroxy-erythromycin A

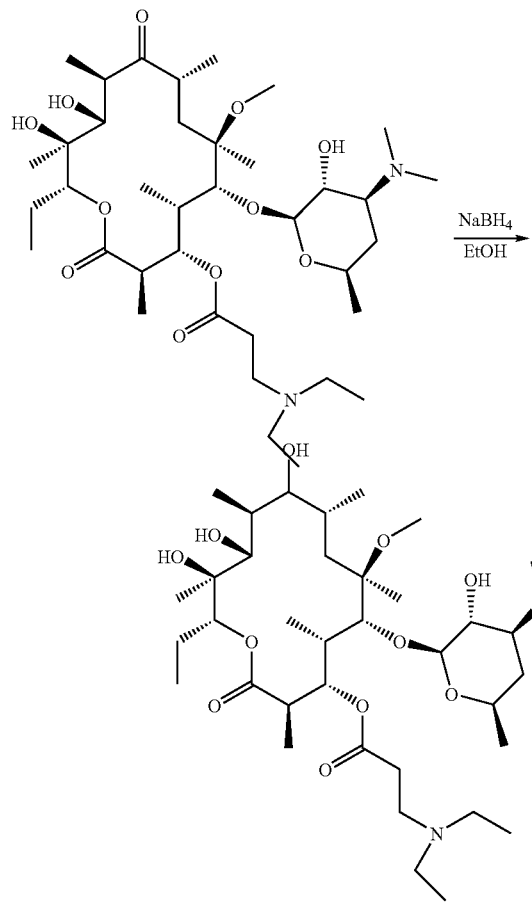

A solution of the compound formed in Example 5 (35 mg, 0.05 mmol) and NaBH$_4$ (10 mg, 0.25 mmol) in EtOH (1.5 ml) was stirred overnight at room temperature. The reaction mixture was diluted with 1N HCl (10 ml), stirred for 10 minutes, and the pH was then adjusted to 9.5. The water layer was extracted with DCM (3×15 ml). Combined organic layers were dried over anhydrous Na$_2$SO$_4$. Evaporation of solvent afforded the title compound (20 mg).

MS (ES+) m/z: [MH]$^+$=719.5

What is claimed is:

1. A compound of Formula (I)

(I)

wherein
A is a bivalent radical selected from —C(O)—, —NHC(O)—, —C(O)NH—, —N(R$^7$)CH$_2$—, —CH$_2$N(R$^7$)—, —CH(OH)— and —C(=NOR$^7$)—;
R$^1$ is —OC(O)(CH$_2$)$_n$NR$^8$R$^9$, —O—(CH$_2$)$_n$NR$^8$R$^9$, or —OC(O)CH=CH$_2$;
R$^2$ is hydrogen or a hydroxyl protecting group;
R$^3$ is hydrogen, unsubstituted C$_{1-4}$ alkyl, C$_{1-4}$ alkyl substituted at the terminal carbon atom with a CN or NH$_2$ group, or C$_{1-5}$ alkanoyl;
R$^4$ is hydrogen, C$_{1-4}$ alkyl or C$_{2-6}$ alkenyl;

$R^5$ is hydroxy, methoxy, —OC(O)(CH$_2$)$_n$NR$^8$R$^9$ or —O—(CH$_2$)$_n$NR$^8$R$^9$;

$R^6$ is hydroxy; or $R^5$ and $R^6$ taken together with the intervening atoms form a cyclic group having the following structure:

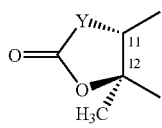

wherein Y is a bivalent radical selected from —CH$_2$—, —CH(CN)—, —O—, —N(R$^7$)— and —CH(SR$^7$)—;

$R^7$ is hydrogen or C$_{1-6}$ alkyl;

$R^8$ is C$_{3-7}$ cycloalkyl or C$_{1-18}$ alkyl, wherein C$_{1-18}$ alkyl is:
  i) uninterrupted or interrupted by from 1 to 3 bivalent radical groups selected from —O—, —S— and —N(R$^7$)—; and/or
  ii) unsubstituted or substituted by from 1 to 3 groups selected from halogen, OH, NH$_2$, N—(C$_1$-C$_6$)alkylamino, N,N-di(C$_1$-C$_6$-alkyl)amino, CN, NO$_2$, OCH$_3$, a C$_{3-8}$ membered non-aromatic ring which is saturated or unsaturated, a heterocyclic non-aromatic ring containing between 2 and 6 carbon atoms which is saturated or unsaturated and contains from 1 to 2 heteroatoms selected from oxygen, sulfur and nitrogen, alkylcarbonylalkoxy and alkoxycarbonylamino;

$R^9$ is hydrogen, C$_{3-7}$ cycloalkyl or C$_{1-18}$ alkyl, wherein C$_{1-18}$ alkyl is:
  i) uninterrupted or interrupted by from 1 to 3 bivalent radical groups selected from —O—, —S— and —N(R$^7$)—; and/or
  ii) unsubstituted or substituted by from 1 to 3 groups selected from halogen, OH, NH$_2$, N—(C$_1$-C$_6$)alkylamino, N,N-di(C$_1$-C$_6$-alkyl)amino, CN, NO$_2$, OCH$_3$, a C$_{3-8}$ membered non-aromatic ring which is saturated or unsaturated, a heterocyclic non-aromatic ring containing between 2 and 6 carbon atoms which is saturated or unsaturated and contains from 1 to 2 heteroatoms selected from oxygen, sulfur and nitrogen, alkylcarbonylalkoxy and alkoxycarbonylamino; or $R^8$ and $R^9$ taken together with the nitrogen to which they are attached form a non-aromatic heterocyclic ring containing between 2 and 6 carbon atoms which is:
  i) saturated or unsaturated and contains 0 or 1 additional heteroatoms selected from oxygen, sulfur and nitrogen; and/or
  ii) unsubstituted or substituted by from 1 to 2 groups selected from C$_{1-5}$ alkanoyl; C$_{1-6}$ alkyl, wherein C$_{1-6}$ alkyl is uninterrupted or is interrupted by 1-3 bivalent radical groups selected from —O—, —S— and —N(R$^7$)—, and/or wherein C$_{1-6}$ alkyl is unsubstituted or substituted by from 1 to 2 groups selected from OH, NH$_2$, a non-aromatic heterocyclic ring containing between 2 and 6 carbon atoms which is unsubstituted or is substituted by a group selected from C$_{1-4}$ alkyl, halogen, NH$_2$, OH, SH, C$_{1-6}$ alkoxy and C$_{1-4}$ hydroxyalkyl, and C$_{3-7}$ cycloalkyl which is unsubstituted or is substituted by a group selected from C$_{1-4}$ alkyl, halogen, NH$_2$, OH, SH, C$_{1-8}$ alkoxy, C$_{1-4}$ hydroxyalkyl; and C$_1$-C$_4$ dialkylamino;

n is an integer from 1 to 8 or a pharmaceutically acceptable salt thereof.

2. A compound according to claim 1, wherein

A is a bivalent radical selected from —C(O)—, —NHC(O)—, —C(O)NH—, —N(R$^7$)CH$_2$—, —CH$_2$N(R$^7$)—, —CH(OH)— and —C(=NOR$^7$)—;

$R^1$ is —OC(O)(CH$_2$)$_n$NR$^8$R$^9$, —O—(CH$_2$)$_n$NR$^8$R$^9$, or —OC(O)CH=CH$_2$;

$R^2$ is hydrogen or a hydroxyl protecting group;

$R^3$ is unsubstituted C1-4 alkyl, C1-4 alkyl substituted at the terminal carbon atom with a CN or NH$_2$ group, or C1-5 alkanoyl;

$R^4$ is hydrogen, C1-4 alkyl or C2-6 alkenyl;

$R^5$ is hydroxy, methoxy, —OC(O)(CH$_2$)$_n$NR$^8$R$^9$ or —O—(CH$_2$)$_n$NR$^8$R$^9$;

$R^6$ is hydroxy; or $R^5$ and $R^6$ taken together with the intervening atoms form a cyclic group having the following structure:

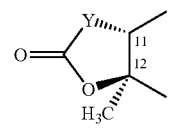

wherein Y is a bivalent radical selected from —CH$_2$—, —CH(CN)—, —O—, —N(R$^7$)— and —CH(SR$^7$)—;

$R^7$ is hydrogen or C$_{1-6}$ alkyl;

$R^8$ is C$_{3-7}$ cycloalkyl or C$_{1-18}$ alkyl, wherein C$_{1-18}$ alkyl is:
  i) uninterrupted or interrupted by from 1 to 3 bivalent radical groups selected from —O—, —S— and —N(R$^7$)—; and/or
  ii) unsubstituted or substituted by from 1 to 3 groups selected from halogen, OH, NH$_2$, N—(C$_1$-C$_6$)alkylamino, N,N-di(C$_1$-C$_6$-alkyl)amino, CN, NO$_2$, OCH$_3$, a C$_{3-8}$ membered non-aromatic ring which is saturated or unsaturated, a heterocyclic non-aromatic ring containing from 2 to 6 carbon atoms which is saturated or unsaturated and contains from 1 to 2 heteroatoms selected from oxygen, sulfur and nitrogen, alkylcarbonylalkoxy and alkoxycarbonylamino;

$R^9$ is hydrogen, C$_{3-7}$ cycloalkyl or C$_{1-18}$ alkyl, wherein C$_{1-18}$ alkyl is:
  uninterrupted or interrupted by from 1 to 3 bivalent radical groups selected from —O—, —S— and —N(R$^7$)—; and/or
  ii) unsubstituted or substituted by from 1 to 3 groups selected from halogen, OH, NH$_2$, N—(C$_1$-C$_6$)alkylamino, N,N-di(C$_1$-C$_6$-alkyl)amino, CN, NO$_2$, OCH$_3$, a C$_{3-8}$ membered non-aromatic ring which is saturated or unsaturated, a heterocyclic non-aromatic ring containing between 2 and 6 carbon atoms which is saturated or unsaturated and contains from 1 to 2 heteroatoms selected from oxygen, sulfur and nitrogen, alkylcarbonylalkoxy and alkoxycarbonylamino; or $R^8$ and $R^9$ taken together with the nitrogen to which they are attached form a non-aromatic heterocyclic ring containing between 2 and 6 carbon atoms which is:
  saturated or unsaturated and contains 0 or 1 additional heteroatoms selected from oxygen, sulfur and nitrogen; and/or
  ii) unsubstituted or substituted by from 1 to 2 groups selected from C$_{1-5}$ alkanoyl; C$_{1-6}$ alkyl, wherein C$_{1-6}$ alkyl is uninterrupted or is interrupted by 1-3 bivalent radical groups selected from —O—, —S— and —N(R$^7$)—, and/or wherein C$_{1-6}$ alkyl is unsubstituted or substituted by from 1 to 2 groups selected from OH, NH$_2$, a non-aromatic heterocyclic ring containing between 2 and 6 carbon atoms which is unsubstituted or is substituted by a group selected from $C_{1-4}$ alkyl, halogen, $NH_2$, OH, SH, $C_{1-6}$ alkoxy and $C_{1-4}$ hydroxyalkyl, and $C_{3-7}$ cycloalkyl which is unsubstituted or is substituted by a group selected from $C_{1-4}$ alkyl, halogen, $NH_2$, OH, SH, $C_{1-6}$ alkoxy, and $C_{1-4}$ hydroxyalkyl;

n is an integer from 1 to 8 or a pharmaceutically acceptable salt thereof.

3. A compound according to claim 1, wherein

A is a bivalent radical selected from —C(O)— and —NHC(O)—;

$R^1$ is —OC(O)(CH$_2$)$_n$NR$^8$R$^9$, or —OC(O)CH=CH$_2$;

$R^2$ is a hydroxyl protecting group;

$R^3$ is unsubstituted $C_{1-4}$ alkyl;

$R^4$ is H or $C_{1-4}$ alkyl;

$R^5$ is hydroxy;

$R^6$ is hydroxy; or $R^5$ and $R^6$ taken together with the intervening atoms form a cyclic group having the following structure:

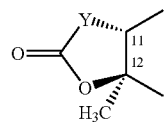

wherein Y is —NH—;

$R^8$ is a $C_{1-18}$ alkyl;

$R^9$ is hydrogen or a $C_{1-18}$ alkyl; and n is an integer from 1 to 8;

or a pharmaceutically acceptable salt thereof.

4. A compound of formula (I)

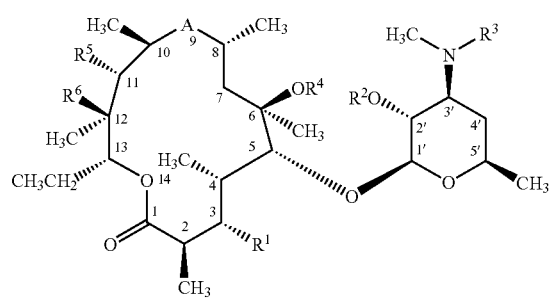

(I)

wherein:

A is —NHC(O)—;

$R^1$ is —OC(O)CH=CH$_2$ or —OC(O)(CH$_2$)$_n$NR$^8$R$^9$;

$R^2$ is H;

$R^3$ is —CH$_3$;

$R^4$ is —CH$_3$;

$R^5$ is hydroxy;

$R^6$ is hydroxy, $R^8$ and $R^9$ are each —CH$_2$CH$_3$; and n is 2;

or a pharmaceutically acceptable salt thereof.

5. A compound according to claim 1, wherein

A is a bivalent radical selected from —C(O)—, —NHC(O)—, —N(R$^7$)CH$_2$—, and —CH(OH)—;

$R^1$ is —OC(O)(CH$_2$)$_n$NR$^8$R$^9$, —O—(CH$_2$)$_n$NR$^8$R$^9$, or —OC(O)CH=CH$_2$;

$R^2$ is hydrogen or a hydroxyl protecting group;

$R^3$ is hydrogen or —CH$_3$;

$R^4$ is hydrogen or —CH$_3$;

$R^5$ is hydroxy;

$R^6$ is hydroxy; or $R^5$ and $R^6$ taken together with the intervening atoms form a cyclic group having the following structure:

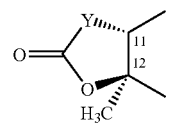

wherein Y is a bivalent radical selected from —O— and —N(R$^7$)—;

$R^7$ is hydrogen, —CH$_3$ or —CH$_2$CH$_3$;

$R^8$ is $C_{1-6}$ alkyl, wherein $C_{1-6}$ alkyl is:
  i) uninterrupted or interrupted by the bivalent radical group —N(R$^7$)—; and/or
  ii) unsubstituted or substituted by an —OH group;

$R^9$ is hydrogen or $C_{1-6}$ alkyl, wherein $C_{1-6}$ alkyl is:
  i) uninterrupted or interrupted by the bivalent radical group —N(R$^7$)—; and/or
  ii) unsubstituted or substituted by an —OH group; or $R^8$ and $R^9$ taken together with the nitrogen to which they are attached form a non-aromatic heterocyclic ring containing between 2 and 6 carbon atoms which is:
  i) saturated and contains 1 additional nitrogen heteroatom; and
  (ii) is substituted by one $C_{1-6}$ alkyl, wherein $C_{1-6}$ alkyl is uninterrupted or is interrupted by one bivalent —N(R$^7$)— radical group, and wherein $C_{1-6}$ alkyl is unsubstituted or substituted by one unsubstituted heterocyclic ring containing between 2 and 6 carbon atoms, or by $C_{1-4}$ dialkylamino;

n is an integer from 1 to 3;

or a pharmaceutically acceptable salt thereof.

6. A compound according to claim 5, wherein $R^2$ is an hydroxyl protecting group having the formula —C(O)CH$_3$.

7. A compound according to claim 1 selected from the group consisting of:

3-O-Propenoyl-3-O-decladinosyl-6-O-methyl-9a-aza-9a-homoerythromycin A,

3-O-(3-Diethylamino-propionyl)-3-O-decladinosyl-6-O-methyl-9a-aza-9a-homoerythromycin A, 2'-O-Acetyl-3-O-propenoyl-3-O-decladinosyl-6-O-methyl-erythromycin A, 3-O-Propenoyl-3-O-decladinosyl-6-O-methyl-erythromycin A, 3-O-(3-Diethylamino-propionyl)-3-O-decladinosyl-6-O-methyl-erythromycin A, 2'-O-Acetyl-6-O-methyl-3-O-propenoyl-3-O-decladinosyl-erythromycin A 11,12-cyclic carbamate, 6-O-Methyl-3-O-propenoyl-3-O-decladinosyl-erythromycin A 11,12-cyclic carbamate, 6-O-Methyl-3-O-(3-diethylamino-propionyl)-3-O-decladinosyl-erythromycin A 11,12-cyclic carbamate, 3-O-Propenoyl-3-O-decladinosyl-3'-N-demethyl-6-O-methyl-9a-aza-9a-homoerythromycin A, 3-O-(3-Diethylamino-propionyl)-3-O-decladinosyl-3'-N-demethyl-6-O-methyl-9a-aza-9a-homoerythromycin A, 3-O-Propenoyl-3-O-decladinosyl-azithromycin,
3-O-(3-Diethylamino-propionyl)-3-O-decladinosyl-azithromycin,
3-O-(2-Diethylamino-acetyl)-3-O-decladinosyl-azithromycin,
3-O-(2-Diethylamino-acetyl)-3-O-decladinosyl-6-O-methyl-9a-aza-9a-homoerythromycin A,
6-O-Methyl-3-O-decladinosyl-3-O-(3-diethylaminopropyl)-9a-aza-9a-homoerythromycin A,
6-O-Methyl-3-O-decladinosyl-3-O-{3-[4-(2-diethylamino-ethyl)-piperazin-1-yl]-propionyl}-9a-aza-9a-homoerythromycin A,
6-O-Methyl-3-O-decladinosyl-3-O-{3-[4-(2-dimethylamino-ethyl)-piperazin-1-yl]-propionyl}-9a-aza-9a-homoerythromycin A,
6-O-Methyl-3-O-decladinosyl-3-O-[3-(3-dimethylamino-propylamino)-propionyl]-9a-aza-9a-homoerythromycin A,
6-O-Methyl-3-O-decladinosyl-3-O-[3-(2-dimethylamino-ethylamino)-propionyl]-9a-aza-9a-homoerythromycin A,
6-O-Methyl-3-O-decladinosyl-3-O-{3-[4-(3-diethylamino-propyl)-piperazin-1-yl]-propionyl}-9a-aza-9a-homoerythromycin A,
6-O-Methyl-3-O-decladinosyl-3-O-{3-[(2-hydroxy-ethyl)-methyl-amino]-propionyl}-9a-aza-9a-homoerythromycin A,
6-O-Methyl-3-O-decladinosyl-3-O{3-[4-(3-pyrrolidin-1-yl-propyl)-[1,4]diazepan-1-yl]-propionyl}-9a-aza-9a-homoerythromycin A,
6-O-Methyl-3-O-decladinosyl-3-O-[3-(3-diethylamino-propylamino)-propionyl]-9a-aza-9a-homoerythromycin A,
6-O-Methyl-3-O-decladinosyl-3-O-[3-(2-diethylamino-ethylamino)-propionyl]-9a-aza-9a-homoerythromycin A, and
3-O-(3-Diethylamino-propionyl)-3-O-decladinosyl-6-O-methyl-9-deoxo-9-dihydro-9-hydroxy-erythromycin A,
and pharmaceutically acceptable salts thereof.

8. A process for the preparation of a compound of Formula (I) according to claim 1

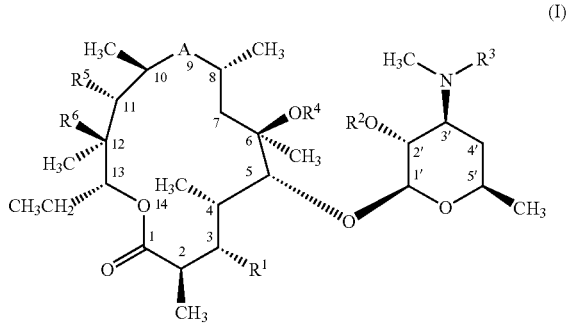

(I)

or a pharmaceutically acceptable salt thereof, which comprises one of the following steps (a)-(g):

a) reacting a compound of Formula (II)

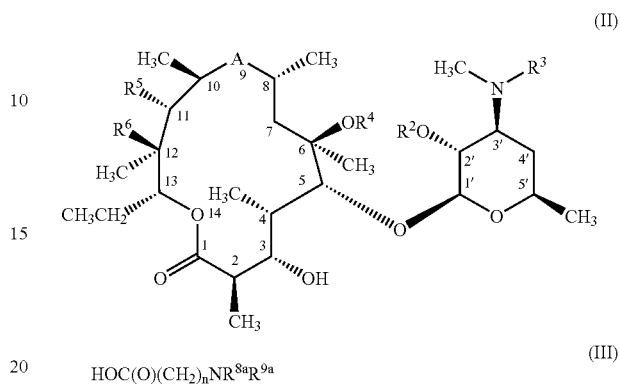

(II)

$HOC(O)(CH_2)_n NR^{8a}R^{9a}$ (III)

with a carboxylic acid of Formula (III) or an activated derivative of a carboxylic acid of Formula (III), wherein $R^2$ is a hydroxyl protecting group, and $R^{8a}$ and $R^{9a}$ are $R^8$ and $R^9$ as defined in claim 1 or groups convertible to $R^8$ and $R^9$ as defined in claim 1, to produce a compound of Formula (I), wherein $R^1$ is $-OC(O)(CH_2)_n NR^8R^9$ and n is an integer from 1 to 8;

b) reacting a compound of formula (IV), wherein n is an integer from 1 to 8 and L is a suitable leaving group, with $HNR^{8a}R^{9a}$ (V), wherein $R^{8a}$ and $R^{9a}$ are $R^8$ and $R^9$ as defined in claim 1 or groups convertible to $R^8$ and $R^9$ as defined in claim 1, to produce a compound of Formula (I) wherein $R^1$ is $-OC(O)(CH_2)_n NR^8R^9$ and n is an integer from 1 to 8;

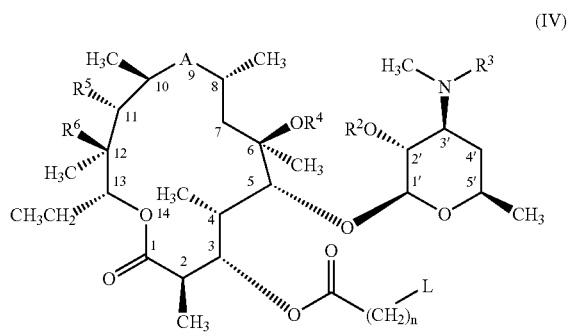

(IV)

c) reacting a compound of formula (VII) with a compound of formula $HNR^{8a}R^{9a}$ (V), wherein $R^{8a}$ and $R^{9a}$ are $R^8$ and $R^9$ as defined in claim 1 or groups convertible to $R^8$ and $R^9$ as defined in claim 1, to produce a compound of Formula (I) wherein $R^1$ is $-OC(O)(CH_2)_n NR^8R^9$ and n is 2;

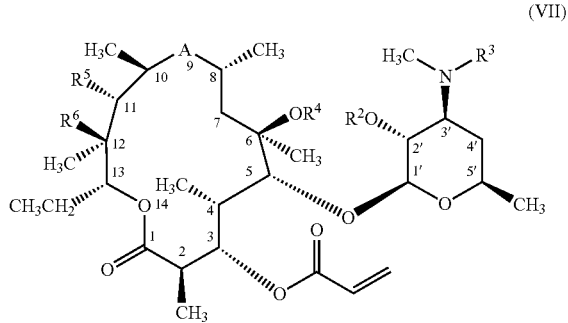

(VII)

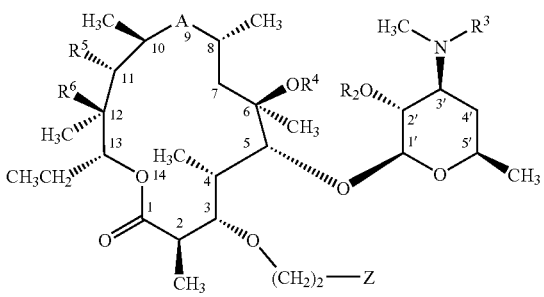

(XI)

d) reacting a compound of Formula (VIII), wherein n is an integer from 1 to 8, with a compound of Formula $HNR^{8a}R^{9a}$ (V), wherein $R^{8a}$ and $R^{9a}$ are $R^8$ and $R^9$ as defined in claim 1 or groups convertible to $R^8$ and $R^9$ as defined in claim 1, to produce a compound of Formula (I) wherein $R^1$ is $—O—(CH_2)_nNR^8R^9$ and n is an integer from 1 to 8;

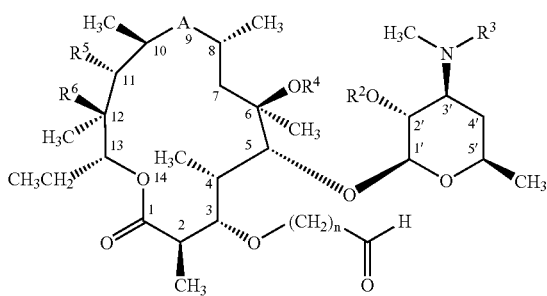

(VIII)

e) reacting a compound of Formula (X), wherein n is an integer from 2 to 8 and L is suitable leaving group, with a compound of Formula $HNR^{8a}R^{9a}$ (V), wherein $R^{8a}$ and $R^{9a}$ are $R^8$ and $R^9$ as defined in claim 1 or groups convertible to $R^8$ and $R^9$ as defined in claim 1, to produce a compound of Formula (I) wherein $R^1$ is $—O—(CH_2)_n NR^8R^9$ and n is an integer from 2 to 8;

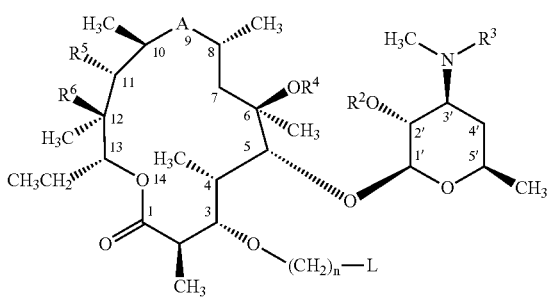

(X)

f) reacting a compound of Formula (II) with acrylonitrile to produce a compound of Formula (XI), wherein Z is cyano group, followed by catalytic reduction of the cyano group to produce a compound of Formula (XI), wherein Z is $—CH_2NH_2$; or g) reacting a compound of Formula (XI), wherein Z is $—CH_2NH_2$ with a compound of Formula $HC(O)R^8$ (XII), to produce a compound of Formula (I) wherein $R^1$ is $—O—(CH_2)_nNR^8R^9$, and $R^8$ and $R^9$ are the same and have the meaning as defined in claim 1, and n is 3;

and thereafter, if required, subjecting the resulting compound to one or more of the following steps:
  i) removal of the protecting group $R^2$,
  ii) conversion of $R^{8a}$ and $R^{9a}$ to $R^8$ and $R^9$, or
  iii) conversion of the compound of Formula (I) into a pharmaceutically acceptable salt thereof.

9. A pharmaceutical composition comprising a compound according to claim 1 or a pharmaceutically acceptable salt thereof, and a pharmaceutically acceptable diluent or carrier.

10. A method of treating an inflammatory disease, disorder or condition characterized by or associated with an undesirable inflammatory immune response, or induced by or associated with excessive secretion of TNF-α, IL-1, IL-6, IL-8, IL-2 or IL-5, which comprises administering to a subject an amount of a compound according to claim 1 effective to reduce or inhibit said inflammatory response.

11. A method of treating an inflammatory condition, or an immune or anaphylactic disorder associated with infiltration of leukocytes into inflamed tissue in a subject which comprises administering to said subject an amount of a compound according to claim 1 effective to inhibit or reduce said infiltration.

12. The method according to claim 10, wherein said inflammatory disease, disorder or condition is selected from the group consisting of asthma, chronic obstructive pulmonary disease (COPD), diffuse panbronchiolitis, adult respiratory distress syndrome, inflammatory bowel disease, Crohn's disease, bronchitis, and cystic fibrosis.

13. The method according to claim 10, wherein said inflammatory disease, disorder or condition is an inflammatory disease, disorder or condition of the lungs, joints, eyes, bowel, skin, or heart.

14. The method according to claim 10, wherein said inflammatory disease, disorder or condition is selected from the group consisting of asthma, adult respiratory distress syndrome, bronchitis, bronchiectasis, bronchiolitis obliterans, diffuse panbronchiolitis, cystic fibrosis, rheumatoid arthritis, rheumatoid spondylitis, osteoarthritis, osteomyelitis, sinusitis, nasal polyps, gouty arthritis, uveitis, conjunctivitis, inflammatory bowel conditions, Crohn's disease, ulcerative colitis, distal proctitis, acne, psoriasis, eczema, dermatitis, coronary infarct damage, coronary artery disease, chronic inflammation, endotoxin shock, and smooth muscle proliferation disorders.

15. A method of treating an inflammatory disease, disorder or condition characterized by or associated with excessive unregulated production of a cytokine or inflammatory mediator, which comprises administering to a subject in need thereof an amount of a compound according to claim 1 effective to reduce or inhibit T-cell proliferation or cytokine production.

16. A method of inhibiting one or more inflammatory processes selected from the group consisting of proinflammatory cytokine production and lymphocyte proliferation comprising exposing an organ or tissue afflicted with inflammation to an amount of a compound according to claim 1 effective to inhibit said inflammatory process.

17. A method for inhibiting pro-inflammatory cytokine production comprising exposing human peripheral leukocytes to an amount of a compound according to claim 1 effective to reduce production of at least one of TNF-α, IL-1, IL-6, IL-8, IL-2 or IL-5 compared to control leukocytes.

18. A method for inhibiting human T-cell proliferation comprising exposing human T-cells to an amount of a compound according to claim 1 effective to reduce production of said T-cells compared to control T-cells not exposed to said compound.

19. A method of inhibiting one or more inflammatory processes, wherein the inflammatory process comprises proinflammatory cytokine production, comprising exposing human peripheral leukocytes to an amount of a compound according to claim 1 effective to reduce production of at least one of TNF-α, IL-1, IL-6, IL-8, IL-2 or IL-5 compared to control leukocytes.

20. The method of claim 19, wherein the production of TNF-α is reduced.

21. The method of claim 19, wherein the production of IL-1α and/or IL-1β is reduced.

22. The method of claim 19, wherein the production of IL-2 and/or IL-5 is reduced.

23. The method of claim 16, wherein the inflammatory process comprises lymphocyte proliferation.

24. The method of claim 16, wherein the immune response to an antigen is inhibited.

25. The method of claim 16, wherein the inhibition of the inflammatory process comprises inhibiting the production of cytokines or the proliferation of lymphocytes by at least 50%.

\* \* \* \* \*